(12) United States Patent
Kasugai et al.

(10) Patent No.: US 12,336,755 B2
(45) Date of Patent: Jun. 24, 2025

(54) HAIR CUTTING DEVICE AND HAIR CUTTING SYSTEM

(71) Applicant: Panasonic Intellectual Property Management Co., Ltd., Osaka (JP)

(72) Inventors: Hideki Kasugai, Shiga (JP); Kenji Narita, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 454 days.

(21) Appl. No.: 17/773,786

(22) PCT Filed: Aug. 28, 2020

(86) PCT No.: PCT/JP2020/032540
§ 371 (c)(1),
(2) Date: May 2, 2022

(87) PCT Pub. No.: WO2021/090558
PCT Pub. Date: May 14, 2021

(65) Prior Publication Data
US 2022/0387104 A1  Dec. 8, 2022

(30) Foreign Application Priority Data
Nov. 7, 2019  (JP) ................. 2019-202759

(51) Int. Cl.
*A61B 18/20* (2006.01)
*A61B 17/00* (2006.01)
(Continued)

(52) U.S. Cl.
CPC .. *A61B 18/203* (2013.01); *A61B 2017/00752* (2013.01); *A61B 2018/00761* (2013.01);
(Continued)

(58) Field of Classification Search
None
See application file for complete search history.

(56) References Cited

U.S. PATENT DOCUMENTS 5,820,625 A  10/1998  Zawa et al.
6,572,637 B1 *  6/2003  Yamazaki .............. A61B 18/20
606/9

(Continued)

FOREIGN PATENT DOCUMENTS

CN  104918571 A  9/2015
CN  105188463 A  12/2015
(Continued)

OTHER PUBLICATIONS

English Translation of Chinese Search Report dated Mar. 26, 2024 for the related Chinese Patent Application No. 202080077692.3.
(Continued)

*Primary Examiner* — Benjamin J Klein
*Assistant Examiner* — Willow Grace Welch
(74) *Attorney, Agent, or Firm* — Rimon P.C.

(57) ABSTRACT

A hair cutting device according to the present disclosure comprises an optical waveguide. The optical waveguide comprises a light irradiator. The light irradiator irradiates hair protruding from the skin with light to cut the hair. The refractive index of the light irradiator is smaller than the refractive index of the surface of the skin. As a result, options such as the material of the optical waveguide and the like can be increased. Furthermore, for example, when the skin is appropriately irradiated with light from the light irradiator, an action on the skin such as sterilization or activation can also be expected.

9 Claims, 16 Drawing Sheets

(51) Int. Cl.
*A61B 18/00* (2006.01)
*A61B 18/22* (2006.01)

(52) U.S. Cl.
CPC ............... *A61B 2018/2205* (2013.01); *A61B 2018/2244* (2013.01)

(56) References Cited

U.S. PATENT DOCUMENTS

| | | |
|---|---|---|
| 2014/0276685 A1 | 9/2014 | Gustavsson et al. |
| 2015/0223889 A1 | 8/2015 | Gustavsson et al. |
| 2015/0359592 A1 | 12/2015 | Moeskops et al. |
| 2017/0209214 A1 | 7/2017 | Gustavsson et al. |
| 2018/0344404 A1* | 12/2018 | Bourquin ............. A61B 18/203 |
| 2020/0069370 A1* | 3/2020 | Boamfa ............... A61B 18/203 |

FOREIGN PATENT DOCUMENTS

| | | |
|---|---|---|
| JP | 03036232 U | 4/1997 |
| JP | 2016-514491 A | 5/2016 |
| JP | 2019-505272 A | 2/2019 |
| WO | WO2014143670 A1 | 9/2014 |
| WO | 2017/079339 A1 | 5/2017 |
| WO | 2017/108639 A1 | 6/2017 |

OTHER PUBLICATIONS

Hui Li et al., "Optical Refractive Index in Biological Tissue Optics", vol. 29, Issue 1, p. 55, Feb. 28, 1999.
International Search Report dated Oct. 6, 2020 issued in International Patent Application No. PCT/JP2020/032540, with English translation.
The EPC Office Action dated Nov. 22, 2022 for the related European Patent Application No. 20885060.2.

\* cited by examiner

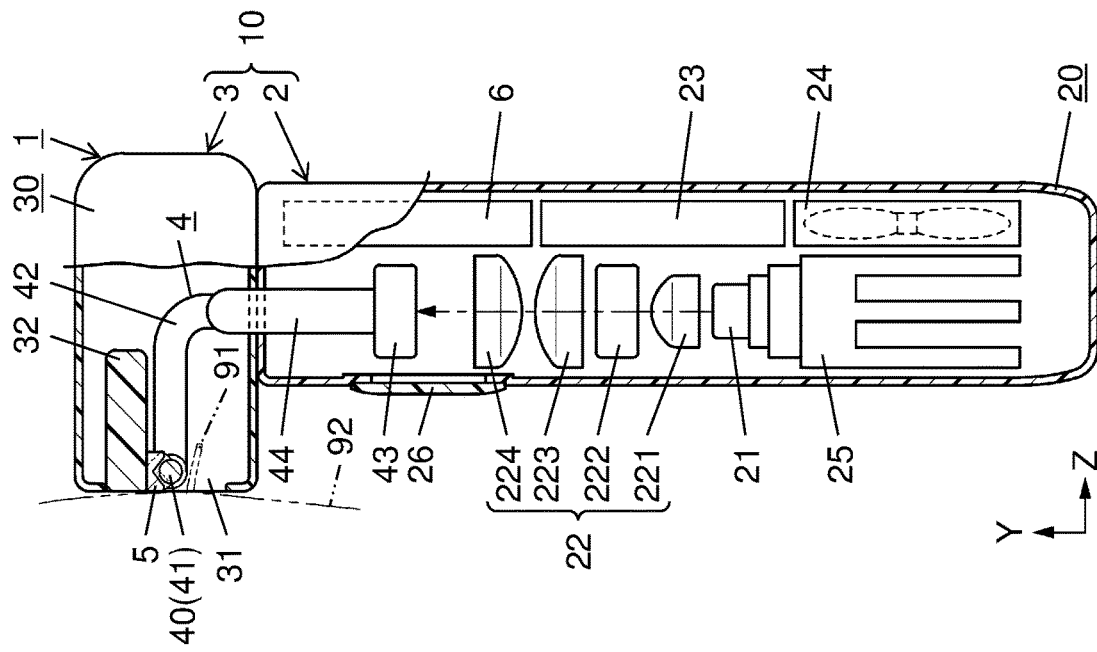
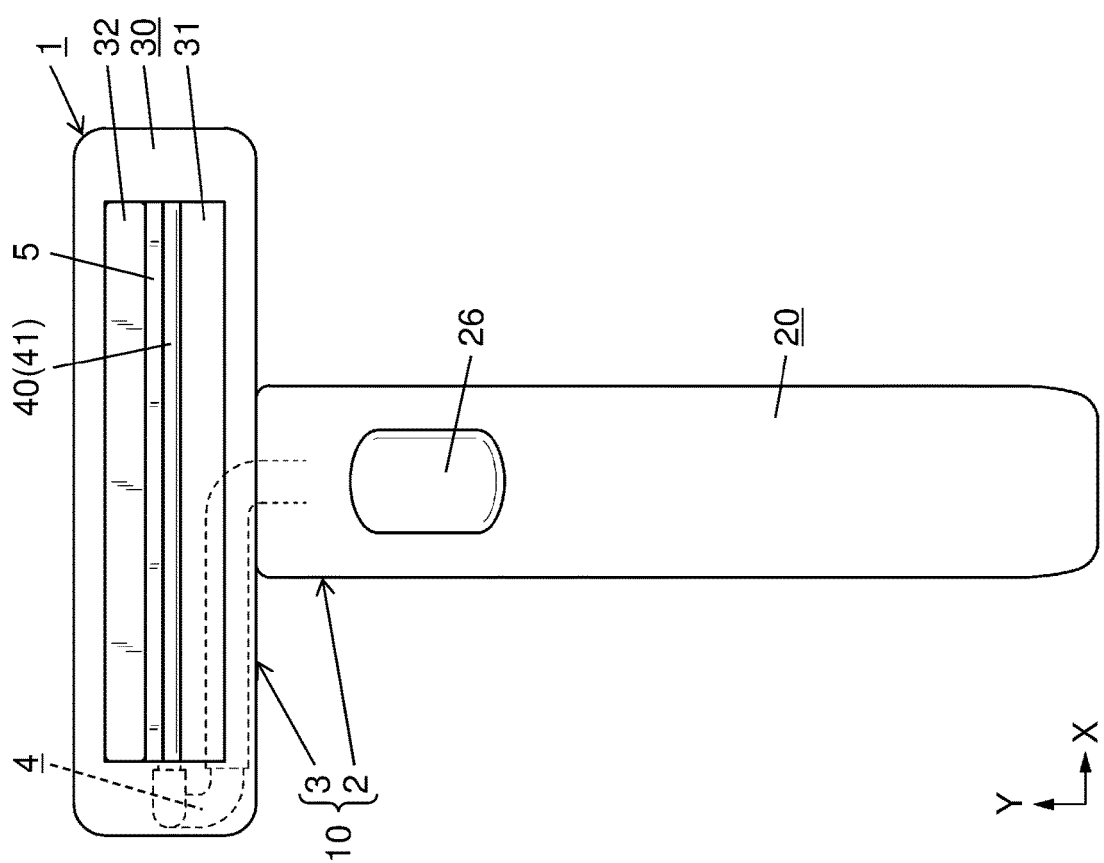

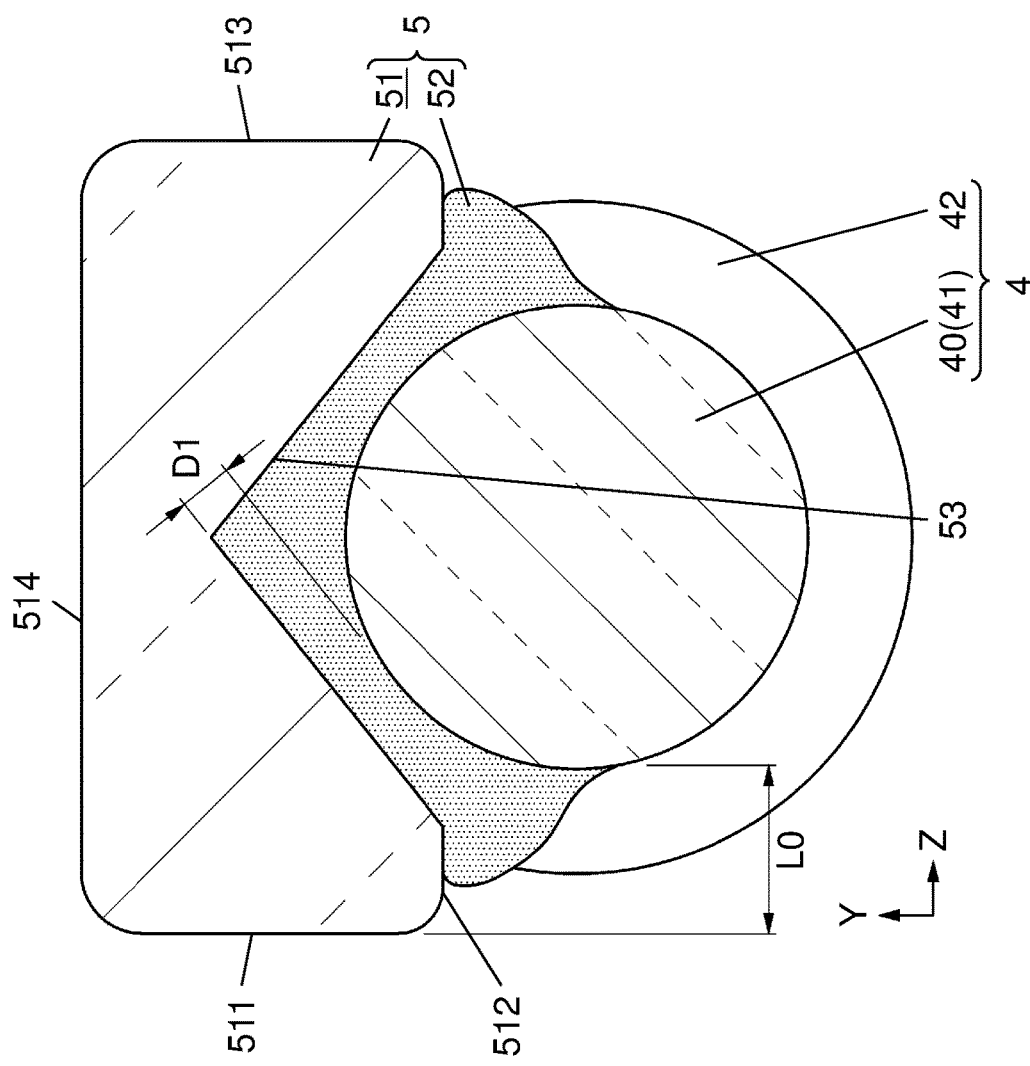
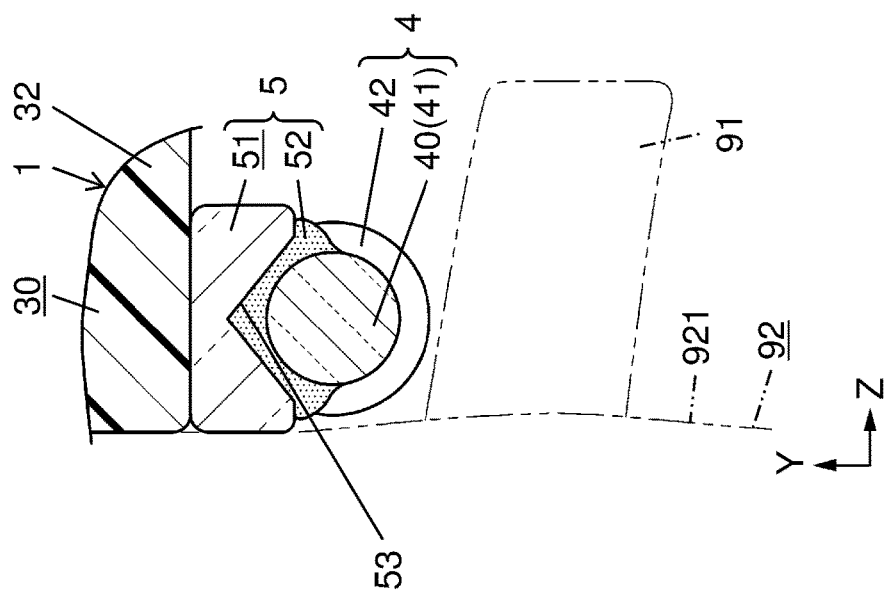

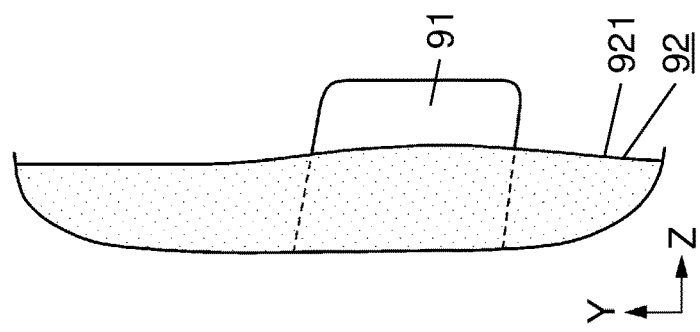
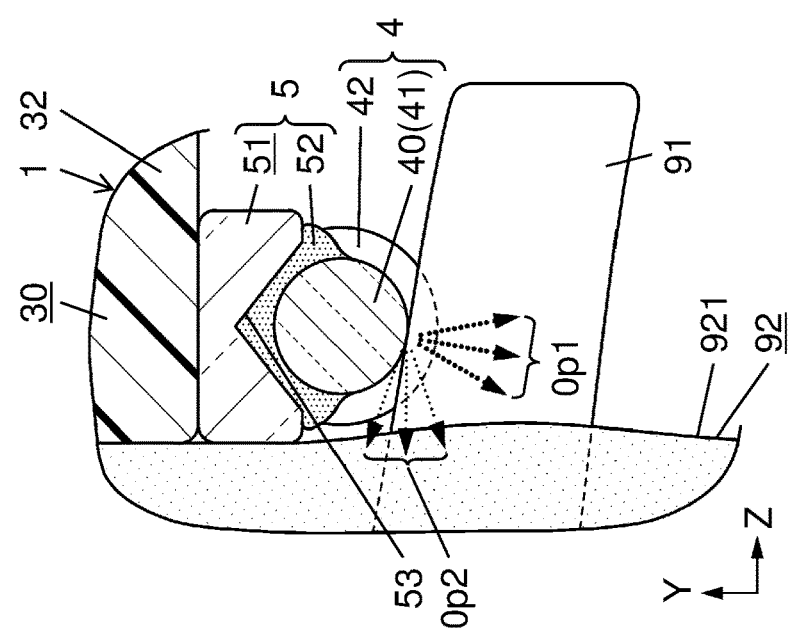
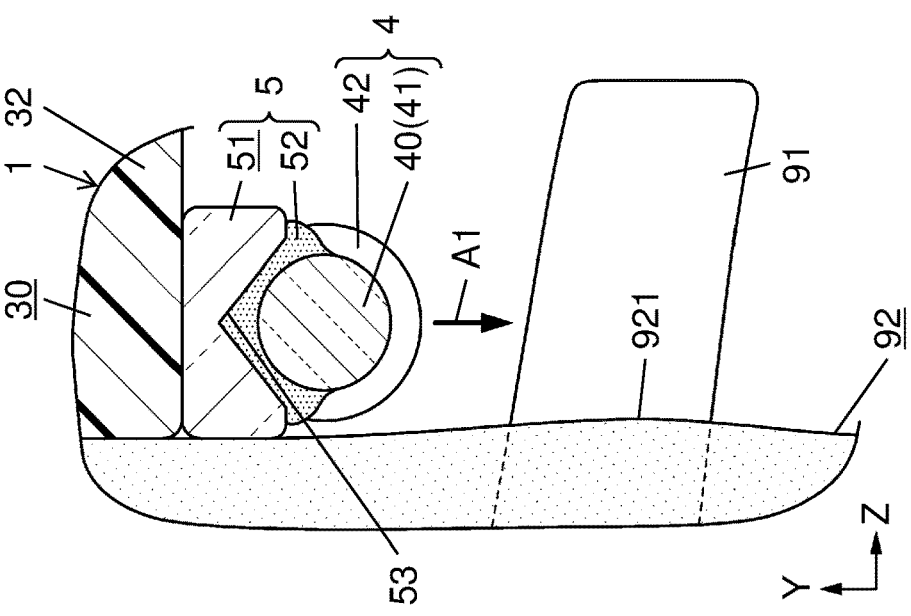

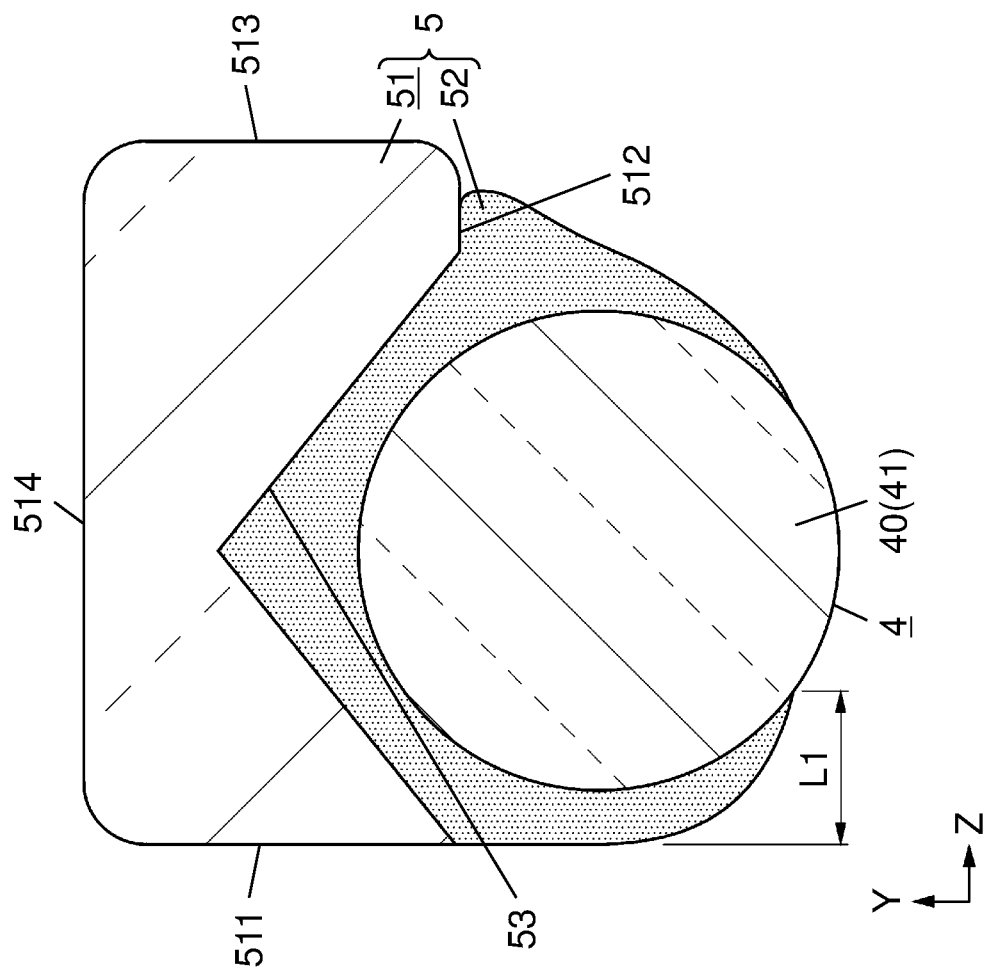
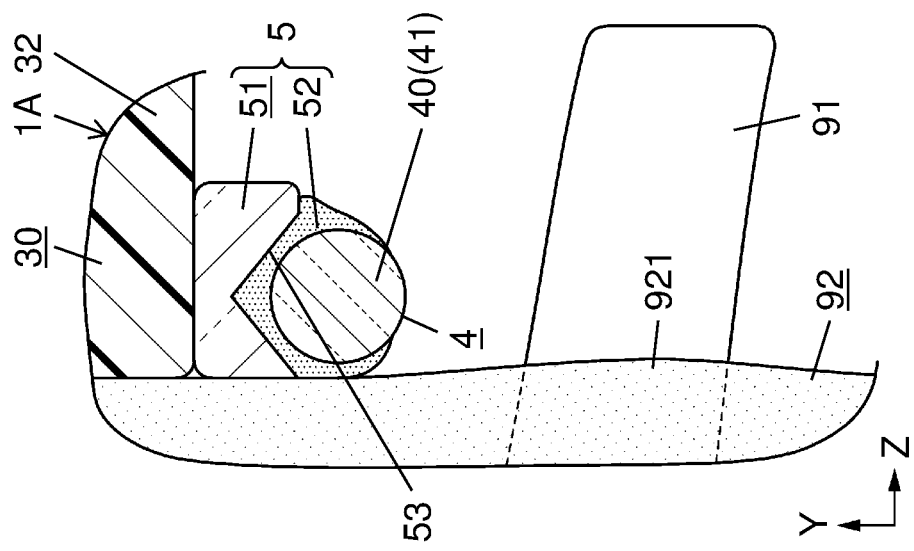

FIG. 11A
FIG. 11B
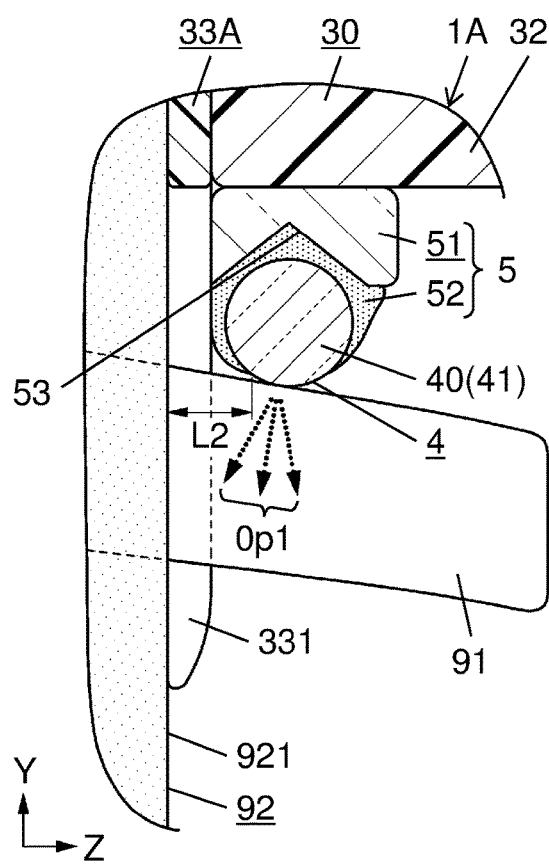
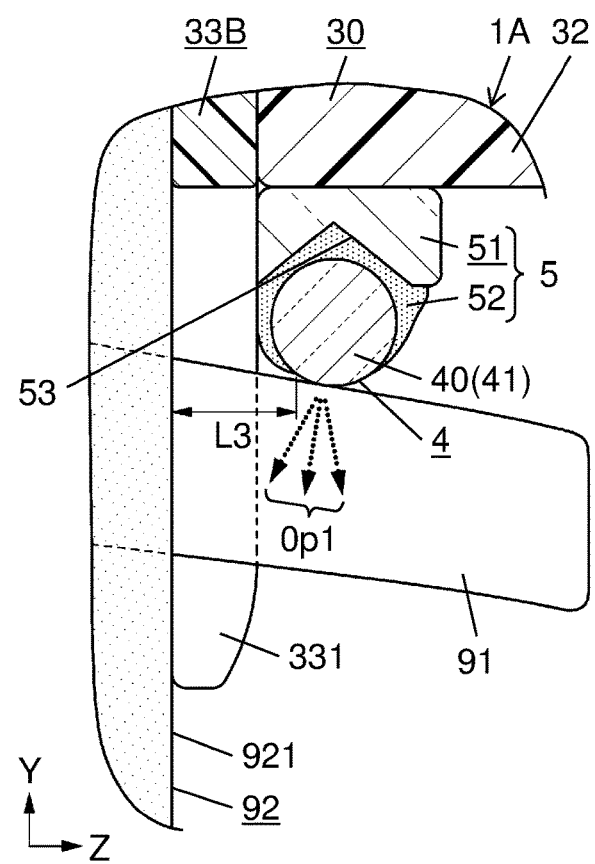

HAIR CUTTING DEVICE AND HAIR CUTTING SYSTEM

CROSS-REFERENCE OF RELATED APPLICATIONS

This application is the U.S. National Phase under 35 U.S.C. § 371 of International Patent Application No. PCT/JP2020/032540, filed on Aug. 28, 2020, which in turn claims the benefit of Japanese Patent Application No. 2019-202759, filed on Nov. 7, 2019, the entire disclosures of which Applications are incorporated by reference herein.

TECHNICAL FIELD

The present disclosure relates generally to a hair cutting device and a hair cutting system, and more particularly to a hair cutting device and a hair cutting system that cut hair by causing light to act on the hair.

BACKGROUND ART

PTL 1 describes a device configured to cut hair using laser light. The device described in PTL 1 includes a laser light source and a fiber optical system. The laser light source is configured to generate laser light having a wavelength selected to target a predetermined chromophore for effectively cutting hair. The fiber optical system has a proximal end, a distal end, an outer wall, and a cutting region disposed toward the distal end and extending along a part of a sidewall. The fiber optical system receives laser light from the laser light source at the proximal end and guides the laser light from the proximal end toward the distal end, and, when the cutting region comes into contact with the hair, emits light from the cutting region toward the hair.

CITATION LIST

Patent Literature

PTL 1: Unexamined Japanese Patent Publication No. 2016-514491

SUMMARY OF THE INVENTION

However, the configuration described in PTL 1 requires improvement in practical use of the hair cutting device using light.

The present disclosure has been made in view of the above circumstances, and an object of the present disclosure is to provide an improved hair cutting device and hair cutting system.

A hair cutting device according to one aspect of the present disclosure comprises an optical waveguide. The optical waveguide comprises a light irradiator. The light irradiator irradiates hair protruding from a skin with light to cut the hair. A refractive index of the light irradiator is smaller than a refractive index of a surface of the skin.

A hair cutting system according to an aspect of the present disclosure comprises the hair cutting device and a light source for generating light to be input to the optical waveguide.

According to the present disclosure, there is an advantage of providing an improved hair cutting device and hair cutting system.

BRIEF DESCRIPTION OF THE DRAWINGS

FIG. 1A is a front view illustrating a configuration of a hair cutting system according to a first exemplary embodiment.

FIG. 1B is a partially broken side view illustrating the configuration of the hair cutting system.

FIG. 2A is a schematic sectional view illustrating a configuration of a main part of the hair cutting device according to the first exemplary embodiment.

FIG. 2B is an enlarged view of the main part of FIG. 2A.

FIG. 3A is a schematic sectional view illustrating an operation of the hair cutting device at the time of cutting hair, particularly a scene before irradiating the hair with light.

FIG. 3B is a schematic sectional view illustrating an operation of the hair cutting device at the time of cutting hair, particularly a scene of irradiating the hair with light.

FIG. 3C is a schematic sectional view illustrating an operation of the hair cutting device at the time of cutting hair, particularly a scene after cutting the hair.

FIG. 10A is a schematic sectional view illustrating a configuration of a main part of a hair cutting device according to a second exemplary embodiment.

FIG. 10B is an enlarged view of the main part of FIG. 10A.

FIG. 11A is a schematic sectional view illustrating a configuration of a main part of a hair cutting device according to a modification of the second exemplary embodiment.

FIG. 11B is a schematic sectional view illustrating a configuration of a main part of the hair cutting device according to another modification of the second exemplary embodiment.

DESCRIPTION OF EMBODIMENT

First Exemplary Embodiment (1) Outline

Figure 4A:
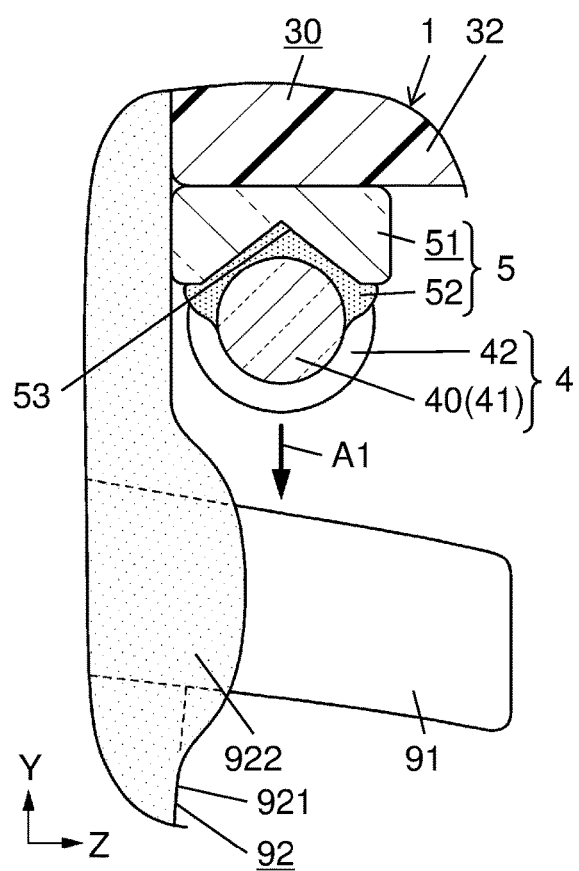
FIG. 4A is a schematic sectional view illustrating an operation of the hair cutting device at the time of cutting hair, particularly a scene before irradiating the hair with light.

An outline of hair cutting device 1 and hair cutting system 10 according to the present exemplary embodiment will be described below with reference to FIGS. 1A to 2B. Hair cutting device 1 is a device that cuts hair 91 by causing light to act on hair 91. Hair 91 to be cut by hair cutting device 1 is, for example, "facial hair" of a human, but is not limited to "facial hair" and includes various hairs protruding from skin 92 of a human and the like. In FIGS. 1B, 2A, and 2B, hair 91 and skin 92 are indicated by imaginary lines (two-dot chain lines).

In short, unlike general "razors" or "scissors" that cut hair 91 with a physical "blade", hair cutting device 1 and hair cutting system 10 cut hair 91 by applying hair 91 light energy instead of the "blade". Therefore, hair cutting device 1 and hair cutting system 10 are less likely to damage skin 92 and the like around hair 91, and are less likely to be physically deteriorated such as nicks and chips, as compared with general "razors" or "scissors".

As illustrated in FIGS. 1A and 1B, hair cutting system 10 according to the present exemplary embodiment includes grip 2 and head 3. Grip 2 includes light source 21 (see FIG. 1B) that generates light. Head 3 includes optical waveguide 4 and holding member 5. Optical waveguide 4 includes light receiver 43 (see FIG. 1B) in grip 2, and the light generated by light source 21 is input to light receiver 43 of optical waveguide 4, whereby the light is transmitted in optical waveguide 4. In the present exemplary embodiment, as an example, light source 21 is a laser light source, and light transmitted in optical waveguide 4 is laser light.

Here, optical waveguide 4 includes light irradiator 40. Optical waveguide 4 cuts hair 91 by irradiating hair 91 with light from light irradiator 40. Holding member 5 holds optical waveguide 4 in head 3. Hair cutting device 1 cuts hair 91 by irradiating hair 91 to be cut with light from light irradiator 40 of optical waveguide 4. Specifically, by bringing light irradiator 40 having a refractive index close to a refractive index of hair 91 to be cut into contact with hair 91, hair cutting device 1 causes light leakage from light irradiator 40 to hair 91, and cuts hair 91 with energy of the light.

In the present exemplary embodiment, a part of hair cutting system 10 corresponding to head 3 constitutes hair cutting device 1. In other words, hair cutting device 1 according to the present exemplary embodiment includes optical waveguide 4 and holding member 5. Head 3 corresponding to hair cutting device 1 constitutes hair cutting system 10 together with grip 2 including light source 21. In other words, hair cutting system 10 according to the present exemplary embodiment includes hair cutting device 1 and light source 21. Light source 21 generates light to be input to optical waveguide 4.

In the present exemplary embodiment, hair cutting device 1 includes optical waveguide 4, and optical waveguide 4 includes light irradiator 40. Light irradiator 40 irradiates hair 91 protruding from skin 92 with light to cut hair 91. Here, the refractive index of light irradiator 40 is smaller than the refractive index of surface 921 (see FIG. 2A) of skin 92.

According to this configuration, since the refractive index of light irradiator 40 is smaller than the refractive index of surface 921 of skin 92, options such as the material of optical waveguide 4 including light irradiator 40 increase, and hair cutting device 1 becomes easily achieved. Furthermore, according to this hair cutting device 1, for example, when skin 92 is appropriately irradiated with light from light irradiator 40, an action on skin 92 such as sterilization or activation can also be expected. As a result, there is an advantage of providing improved hair cutting device 1.

In the present exemplary embodiment, hair cutting device 1 includes optical waveguide 4, and optical waveguide 4 includes light irradiator 40. Light irradiator 40 irradiates hair 91 protruding from skin 92 with light to cut hair 91. Here, at least at the time of cutting hair 91, the power density of the light passing through optical waveguide 4 is more than or equal to 50 kW/cm$^2$.

According to this configuration, since the power density of the light passing through optical waveguide 4 at the time of cutting hair 91 is more than or equal to 50 kW/cm$^2$, it is easy to efficiently cut hair 91 with the light with which light irradiator 40 irradiates hair 91. That is, it is possible to apply sufficient light energy for cutting hair 91 from optical waveguide 4 to hair 91, and it is possible to cut hair 91 in a relatively short time. Therefore, for example, there is an advantage of increasing a width such as a thickness or hardness of hair 91 that can be cut, and, as a result, of providing improved hair cutting device 1.

In the present exemplary embodiment, hair cutting device 1 includes optical waveguide 4 and holding member 5 that holds optical waveguide 4. Optical waveguide 4 includes light irradiator 40. Light irradiator 40 irradiates hair 91 protruding from skin 92 with light to cut hair 91. Holding member 5 holds optical waveguide 4 in such an aspect that light irradiator 40 is exposed from at least one face.

According to this configuration, since holding member 5 holds optical waveguide 4 in such an aspect that light irradiator 40 is exposed from at least one face of holding member 5, even if hair 91 or skin 92 comes into contact with light irradiator 40, for example, positional deviation or the like of optical waveguide 4 hardly occurs. That is, for example, at the time of cutting hair 91, even if an external force from hair 91 or skin 92 acts on light irradiator 40, optical waveguide 4 is less likely to be detached or damaged by the external force. As a result, there is an advantage of providing improved hair cutting device 1.

(2) Details

Details of hair cutting device 1 and hair cutting system 10 according to the present exemplary embodiment will be described below with reference to FIGS. 1A to 6.

Hereinafter, as an example, three axes of an X axis, a Y axis, and a Z axis orthogonal to one another are set, and in particular, an axis along the length of light irradiator 40 is referred to as the "X axis" and an axis along the traveling direction of light irradiator 40 is referred to as the "Y axis". The X axis, the Y axis, and the Z axis are all virtual axes, and the arrows indicating "X", "Y", and "Z" in the drawings are merely described for the sake of description, and are not accompanied by entities. These directions are not intended to limit directions of hair cutting device 1 and hair cutting system 10 when used.

(2.1) Definitions

The "hair" referred to in the present disclosure includes various hairs 91 protruding from skin 92, i.e., various hairs extending from skin 92, and includes, for example, various body hairs such as human hairs, facial hairs, eyebrows, leg hairs, nose hairs, or ear hairs. Furthermore, for example, various hairs 91 protruding from skin 92 of mammals such as dogs or cats and other animals are also included in the "hair" referred to in the present disclosure. That is, hair cutting device 1 according to the present exemplary embodiment is a device for cutting these hairs 91. The "skin" referred to in the present disclosure also includes artificial skins and the like. In the present exemplary embodiment, as an example, a case where hair 91 to be cut by hair cutting device 1 is hair protruding from human skin 92, particularly "facial hair" of an adult male will be described. That is, hair 91 to be cut by hair cutting device 1 is hair that has grown from human facial skin 92. Human skin 92 including facial skin 92 is also referred to as "skin".

The "cutting" of hair 91 referred to the present disclosure includes cutting hair 91 in general, and includes, for example, cutting hair 91 at the root (i.e., shaving hair), trimming hair 91 at an appropriate length, and cutting only the tip of hair. Therefore, the "hair cutting device" referred to in the present disclosure includes, for example, a "shaver" or a "hair shaving device", which is a device for shaving hair 91, and a "trimmer", a "hair clipper", or a "scissors", which is a device for cutting the hair at an appropriate length. Furthermore, the "cutting" of hair 91 referred to in the present disclosure includes not only cutting hair 91 into two at a substantially planar cut surface, but also damaging a cut portion of hair 91 and breaking hair 91 at a cut part. In the present exemplary embodiment, as an example, a case where hair cutting device 1 and hair cutting system 10 are "shavers" suitable for cutting (i.e., shaving) hair 91 (facial hair) to be cut at the root will be described.

The "laser light" referred to in the present disclosure means light amplification by stimulated emission of radiation. Examples of light source 21 that generates laser light include a semiconductor laser (laser diode (LD)) using recombination light emission of a semiconductor. The laser light has characteristics of higher coherence, higher output (power density), higher monochromaticity (single wavelength), and higher directivity than those of light generated by a light emitting diode (LED).

The "optical waveguide" referred to in the present disclosure means an optical member that guides light along a desired path by passing the light. Specific examples of the optical waveguide include an optical fiber having a core and a cladding having refractive indices different from each other and having the core covered with the cladding. The optical fiber can guide light along a desired path by passing light into the core using total reflection of light at an interface between the core and the cladding. Here, the optical waveguide is not particularly limited to a transmission path through which a communication signal (optical signal) passes, and generally means an optical member that guides light along the desired path.

The "holding" referred to in the present disclosure means that one of two objects supports the other object such that the two objects continue to maintain a positional relationship with each other. Here, the relative positional relationship between the two objects may slightly change, and one object and the other object may not be firmly fixed together. That is, holding member 5 may hold optical waveguide 4 in an aspect where the positional relationship between optical waveguide 4 and holding member 5 slightly changes.

The "refractive index" referred to in the present disclosure is a value obtained by dividing a light velocity in vacuum by a light velocity in a medium (more precisely, a phase velocity). The refractive index is basically determined depending on substance, and for example, the refractive index of air is "1.0003" and the refractive index of water is "1.3334". Even for the same substance, the refractive index may vary depending on the wavelength of incident light, but in the present disclosure, the refractive index is indicated for light having a wavelength of 404.7 nm (h line of mercury) unless otherwise specified.

The "power density" referred to in the present disclosure means light intensity per unit area (1 $cm^2$). The unit of the power density is "$kW/cm^2$" or "$J/(s \cdot cm^2)$". Even when the distribution of the light intensity varies in a cross section of optical waveguide 4, an average power density averaged over the entire cross section of core 41 is obtained by dividing the light intensity passing through optical waveguide 4 by the sectional area of core 41 of optical waveguide 4. In the present disclosure, unless otherwise specified, the average power density thus obtained is referred to as "power density".

(2.2) Overall Configuration

First, an overall configuration of hair cutting system 10 according to the present exemplary embodiment will be described with reference to FIGS. 1A and 1B.

As described above, hair cutting system 10 includes hair cutting device 1 and light source 21. Hair cutting device 1 includes optical waveguide 4 and holding member 5 that holds optical waveguide 4. Optical waveguide 4 includes light irradiator 40, and outputs light from light irradiator 40 when light generated by light source 21 is input. Hair cutting system 10 cuts hair 91 by inputting light generated by light source 21 to optical waveguide 4 of hair cutting device 1, and irradiating hair 91 from light irradiator 40 of optical waveguide 4 with the light.

More specifically, as the refractive index of light irradiator 40, hair cutting system 10 adopts a value close to the refractive index of hair 91 to be cut. As a result, in a state where hair 91 is in contact with light irradiator 40, light leaks from light irradiator 40 to hair 91, and hair 91 is cut by energy of the light. On the other hand, in a state where hair 91 is not in contact with light irradiator 40 and only air (refractive index: 1.0) is in contact with light irradiator 40, the amount of light leakage from light irradiator 40 can be suppressed to be small by the difference in refractive index between light irradiator 40 and the air.

In the present exemplary embodiment, as described above, hair cutting system 10 includes grip 2 including light source 21 and head 3 constituting hair cutting device 1. As illustrated in FIGS. 1A and 1B, grip 2 includes first case 20, and first case 20 accommodates light source 21 and the like. As an example, first case 20 is formed in a prismatic shape having a length along the Y axis. As illustrated in FIGS. 1A and 1B, head 3 includes second case 30, and second case 30 accommodates optical waveguide 4 and the like. As an example, second case 30 is formed in a prismatic shape having a length along the X axis. In the present exemplary embodiment, one end in the longitudinal direction of first case 20 and a center in the longitudinal direction of second case 30 are coupled with each other, whereby first case 20 and second case 30 constitute a substantially T-shaped case as a whole when viewed from one side of the Z axis.

Thus, hair cutting system 10 having a substantially T-shaped appearance as a whole is used in the same manner as a "T-shaped razor". That is, the user grips grip 2 of hair cutting system 10, i.e., first case 20 with one hand to hold hair cutting system 10 when cutting (shaving) hair 91 (here, "facial hair") to be cut. In this state, the user brings head 3 of hair cutting system 10, i.e., one face of second case 30 in the Z axis direction into contact with skin 92 (of the face) of the user, and moves head 3 in the Y axis direction along skin 92, thereby cutting hair 91 with light irradiator 40 of head 3. At this time, as illustrated in FIG. 1B, the user brings the face of second case 30 facing the negative orientation of the Z axis into contact with skin 92 and moves head 3 in the negative orientation of the Y axis, thereby cutting hair 91 positioned forward (i.e., in the negative orientation of the Y axis) in the traveling direction of head 3.

In the present exemplary embodiment, as an example, both first case 20 and second case 30 are made of synthetic resin. First case 20 and second case 30 are coupled by an appropriate means such as adhesion, welding, bonding, or coupling using a fastening member (screw or the like).

In addition to first case 20 and light source 21, grip 2 further includes control circuit 6, optical system 22, battery 23, fan 24, heat sink 25, and operation unit 26.

Control circuit 6, optical system 22, battery 23, fan 24, and heat sink 25 are all accommodated in first case 20. Operation unit 26 is provided on one face (face facing the negative orientation of the Z axis) of first case 20. Optical waveguide 4 included in head 3 is accommodated across first case 20 and second case 30 such that one end (light receiver 43) of optical waveguide 4 is positioned in first case 20 of grip 2.

Light source 21 converts electrical energy into optical energy to generate light to be input to optical waveguide 4. In the present exemplary embodiment, light source 21 is a laser light source. That is, the light generated by light source 21 is laser light generated by stimulated emission. Here, light source 21 includes a semiconductor laser using recombination light emission of a semiconductor.

The wavelength of light generated by light source 21 is more than or equal to 400 nm. That is, light source 21 generates laser light having a peak wavelength or a dominant wavelength on the longer wavelength side than 400 nm. In the present exemplary embodiment, the wavelength of light generated by light source 21 is less than or equal to 700 nm. Although described in detail in the section of "(3) Action", light having a wavelength in the range from 400 nm to 450 nm inclusive, for example, can be expected to have a sterilizing action on propionibacterium acnes and the like existing on skin 92. Light having a wavelength in the range from 450 nm to 700 nm inclusive can be expected to have an activating action of skin 92.

Control circuit 6 is a circuit that controls at least light source 21. Control circuit 6 supplies power to light source 21 to cause light source 21 to emit light (turn on). Furthermore, control circuit 6 performs switching of on or off of light source 21, adjustment of output (brightness, wavelength, or the like) of light source 21, and the like. Control circuit 6 includes a printed wiring board (substrate) and a plurality of electronic components mounted on the printed wiring board. Control circuit 6 not only controls light source 21 but also fan 24, operation unit 26, and the like. Control circuit 6 will be described in detail in the section of "(2.6) Control circuit".

Optical system 22 is disposed between light source 21 and optical waveguide 4, and guides light from light source 21 to optical waveguide 4. Optical system 22 includes a plurality of lenses. In the example of FIG. 1B, optical system 22 includes first lens 221, second lens 222, third lens 223, and fourth lens 224. However, FIG. 1B does not strictly illustrate the shape and arrangement of individual lenses, and merely schematically illustrates optical system 22.

Battery 23 functions as a power supply that supplies power for driving control circuit 6, light source 21, fan 24, and the like. In the present exemplary embodiment, as an example, battery 23 is a secondary battery such as a lithium ion battery (LIB) that can be charged and discharged.

Fan 24 is a cooling fan for cooling light source 21. Specifically, fan 24 promotes heat dissipation of heat sink 25 by generating an airflow passing through heat sink 25 in first case 20.

Heat sink 25 is made of a material having a relatively high thermal conductivity, for example, aluminum. Heat sink 25 is thermally coupled to light source 21 and mainly radiates heat from light source 21.

Operation unit 26 receives a user's operation and outputs an electric signal responsive to the user's operation to control circuit 6. In the present exemplary embodiment, as an example, operation unit 26 includes at least one mechanical switch such as a push switch or a slide switch.

Head 3 further includes fixing block 32 in addition to second case 30, optical waveguide 4, and holding member 5.

Opening 31 for exposing at least light irradiator 40 to the outside of second case 30 is formed in second case 30 on a face that is in contact with user's skin 92 (i.e., a face facing the negative orientation of the Z axis). Opening 31 is formed in a rectangular shape having a length along the X axis. The inner space and the outer space of second case 30 are connected through opening 31 to each other.

Optical waveguide 4, holding member 5, and fixing block 32 are all accommodated in second case 30. However, as described above, one end (light receiver 43) of optical waveguide 4 is positioned in first case 20 of grip 2. Therefore, the inner space of first case 20 and the inner space of second case 30 are continuous to each other, and optical waveguide 4 is accommodated across first case 20 and second case 30. In the present exemplary embodiment, as an example, in addition to light irradiator 40 of optical waveguide 4, holding member 5 and fixing block 32 are also exposed to the outside of second case 30 through opening 31.

Optical waveguide 4 is an optical member that guides light from light source 21 along a desired path by passing light generated by light source 21. In the present exemplary embodiment, as an example, optical waveguide 4 is an optical fiber. Optical waveguide 4 includes core 41 and cladding 42, and core 41 is covered with cladding 42. Furthermore, in the present exemplary embodiment, as illustrated in FIG. 1B, optical waveguide 4 further includes light receiver 43 and protective sheath 44. Light receiver 43 is accommodated in first case 20 and is disposed so as to oppose optical system 22, thereby taking into optical waveguide 4 the light from light source 21. Specifically, optical waveguide 4 is optically coupled to light source 21 via optical system 22 at light receiver 43 provided at the end of core 41 such that the light from light source 21 propagates through optical waveguide 4 (core 41). Protective sheath 44 is a resin covering member configured to cover cladding 42. That is, the optical fiber used as optical waveguide 4 in the present exemplary embodiment has a triple structure of core 41, cladding 42 positioned outside core 41, and protective sheath 44 positioned outside cladding 42.

Optical waveguide 4 is routed in first case 20 and second case 30 such that at least light receiver 43 is disposed in first case 20 and a region extending from light receiver 43 is routed in second case 30. Optical waveguide 4 has protective sheath 44 only in a portion from one end on light receiver 43 to a first intermediate part, and protective sheath 44 is removed and cladding 42 is exposed in a portion beyond the first intermediate part. Furthermore, optical waveguide 4 has cladding 42 only in a portion from the first intermediate part to a second intermediate part, and cladding 42 is removed and core 41 is exposed in a portion beyond the second intermediate part. In this manner, the region of optical waveguide 4 from which cladding 42 is removed and core 41 is exposed constitutes light irradiator 40.

That is, in the present exemplary embodiment, optical waveguide 4 includes core 41, and light irradiator 40 consists of core 41. In other words, in the present exemplary embodiment, a portion (light irradiator 40) of optical waveguide 4 for cutting hair 91 by irradiating hair 91 with light is formed only of core 41. Optical waveguide 4 will be described in detail in the section of "(2.3) Configuration of hair cutting device".

Holding member 5 is a member that holds optical waveguide 4. Holding member 5 holds at least light irradiator 40 of optical waveguide 4. That is, holding member 5 holds at least a region (light irradiator 40) of optical waveguide 4 where cladding 42 is removed and core 41 is exposed. In the present exemplary embodiment, as an example, only light irradiator 40 is held by holding member 5 in optical waveguide 4, and a region other than light irradiator 40 in optical waveguide 4 is appropriately positionally fixed with a structure other than holding member 5. Holding member 5 is fixed to fixing block 32. Holding member 5 is fixed to fixing block 32 by an appropriate means such as adhesion, welding, bonding, or coupling using a fastening member (screw or the like). As a result, optical waveguide 4 (light irradiator 40) is indirectly fixed to fixing block 32 via holding member 5. Holding member 5 will be described in detail in the section of "(2.4) Holding structure of optical waveguide".

Fixing block 32 is fixed to second case 30. Fixing block 32 is made of synthetic resin and is formed in a prismatic shape having a length along the X axis. Fixing block 32 is fixed to second case 30 by an appropriate means such as adhesion, welding, bonding, or coupling using a fastening member (screw or the like). Holding member 5 is fixed to fixing block 32 as described above. Therefore, optical waveguide 4 (light irradiator 40) is indirectly fixed to second case 30 via holding member 5 and fixing block 32.

Here, in head 3, all of light irradiator 40 of optical waveguide 4, holding member 5, and fixing block 32 are exposed to the outside of second case 30 through opening 31. Specifically, as illustrated in FIGS. 1A and 1B, fixing block 32 is disposed along a length (X axis) of opening 31 in second case 30. Holding member 5 is fixed to a face of fixing block 32 facing forward (negative orientation of the Y axis) in the traveling direction of hair cutting device 1. Moreover, fixing block 32 and holding member 5 are disposed close to a rear side (i.e., positive side of the Y axis) in the travelling direction of hair cutting device 1 so as to secure a gap on a front side in the travelling direction of hair cutting device 1 (head 3) in a shorter direction (Y axis direction) of opening 31.

Fixing block 32 and holding member 5 are disposed such that a face facing the negative orientation of the Z axis is flush with a face of second case 30 facing the negative orientation of the Z axis. Although described in detail in the section of "(2.4) Holding structure of optical waveguide", optical waveguide 4 (light irradiator 40) is fixed to a face of holding member 5 facing forward (negative orientation of Y axis) in the traveling direction of hair cutting device 1.

Although not illustrated in FIGS. 1A and 1B, hair cutting system 10 may further include components such as a charging circuit for battery 23 or a display for displaying an operation state of hair cutting system 10.

(2.3) Configuration of Hair Cutting Device

Next, a more detailed configuration of hair cutting device 1 according to the present exemplary embodiment, i.e., head 3 of hair cutting system 10 will be described with reference to FIGS. 2A and 2B. FIG. 2A is a schematic sectional view illustrating the configuration around optical waveguide 4 and holding structure 5 in hair cutting device 1 (head 3). FIG. 2B is an enlarged view of the main part of FIG. 2A.

In the present exemplary embodiment, a part of hair cutting system 10 corresponding to head 3 constitutes hair cutting device 1. Therefore, second case 30, optical waveguide 4, holding member 5, and fixing block 32 included in head 3 are all components of hair cutting device 1. That is, hair cutting device 1 according to the present exemplary embodiment further includes second case 30 and fixing block 32 in addition to optical waveguide 4 and holding member 5. However, second case 30 and fixing block 32 are not essential components for hair cutting device 1, and at least one of second case 30 and fixing block 32 can be omitted as appropriate.

As described above, optical waveguide 4 in hair cutting device 1 includes light irradiator 40 that irradiates hair 91 with light to cut hair 91. In the present exemplary embodiment, optical waveguide 4 is an optical fiber having core 41 and cladding 42. Cladding 42 covers core 41 over the entire circumference of core 41. Here, both core 41 and cladding 42 have relatively high light transmissivity. However, the refractive index is different between core 41 and cladding 42, and the refractive index of core 41 is larger than the refractive index of cladding 42. With this configuration, the light incident on core 41 from light receiver 43 passes only through core 41 as much as possible due to total reflection or refraction at the interface between core 41 and cladding 42, and reaches the tip end of optical waveguide 4 (end on the opposite side of light receiver 43).

In the present exemplary embodiment, as an example, in optical waveguide 4, both core 41 and cladding 42 are made of synthetic quartz. For example, core 41 is made of synthetic quartz, and cladding 42 is made of synthetic quartz to which an impurity has been added having a refractive index different from that of core 41. In the present exemplary embodiment, as an example, when the fiber incidence numerical aperture (NA) is "0.1", the refractive index of core 41 is "1.4698", and the refractive index of cladding 42 is "1.4309". When the fiber incidence NA is "0.2", the refractive index of core 41 is "1.4698", and the refractive index of cladding 42 is "1.309". The NA and the refractive index mentioned here are merely examples, and are not intended to define a difference between the refractive index of core 41 and the refractive index of cladding 42.

In optical waveguide 4 (optical fiber) having the above-described configuration, a region from the tip end opposite to light receiver 43 to the second intermediate part where cladding 42 is removed and core 41 is exposed constitutes light irradiator 40. That is, in optical waveguide 4, it is core 41 of the region where cladding 42 is removed and core 41 is exposed that constitutes light irradiator 40 that irradiates hair 91 with light.

However, more strictly speaking, in core 41 exposed by removing cladding 42, a region covered with holding member 5 cannot leak light to hair 91, and thus does not function as light irradiator 40 that irradiates hair 91 with light. In other words, in the present exemplary embodiment, light irradiator 40 consists of core 41, and in particular, a region of core 41 that is exposed without being covered with cladding 42 is light irradiator 40. FIGS. 2A and 2B and the like illustrate cross sections at a region of optical waveguide 4 where core 41 is exposed, and an end surface of cladding 42.

In hair cutting device 1 according to the present exemplary embodiment, as described above, the refractive index of light irradiator 40 in optical waveguide 4 is smaller than the refractive index of surface 921 (see FIG. 2A) of skin 92. Here, human skin 92 (skin) includes epidermis, dermis, and subcutaneous tissue. Surface 921 of skin 92 mentioned here means the outermost epidermis of these plurality of elements constituting skin 92 or the surface of the epidermis.

That is, in the present exemplary embodiment, since light irradiator 40 is formed of core 41 of optical waveguide 4 (optical fiber) including core 41 and cladding 42, the refractive index of core 41 is set to be smaller than the refractive index of surface 921 of skin 92. As an example, the refractive index of surface 921 of human skin 92 is assumed to be "1.4770". Then, if the refractive index of core 41, which is light irradiator 40, is "1.4698" as described above, the condition that the refractive index of light irradiator 40 is smaller than the refractive index of surface 921 of skin 92 is satisfied.

More specifically, in the present exemplary embodiment, the refractive index of light irradiator 40 is less than or equal to 1.47. In short, the refractive index of light irradiator 40 is set in a range of less than or equal to "1.4700" so that the refractive index of light irradiator 40 is smaller than the refractive index of surface 921 of skin 92. Thus, even if there is a slight variation in the refractive index of surface 921 of skin 92, the refractive index of light irradiator 40 is smaller than the refractive index of surface 921 of skin 92. That is, even when the refractive index of surface 921 of skin 92 is slightly smaller than "1.4770", the condition that the refractive index of light irradiator 40 is smaller than the refractive index of surface 921 of skin 92 can be satisfied.

Furthermore, the refractive index of surface 921 of skin 92 is smaller than the refractive index of hair 91. That is, when the refractive indices of the three of surface 921 of skin 92, hair 91, which is to be cut and protrudes from skin 92, and light irradiator 40 (core 41) are compared, the refractive index of hair 91 is the largest, the refractive index of surface 921 of skin 92 is the second largest, and the refractive index of light irradiator 40 is the smallest. As an example, the refractive index of human hair 91 (here, "facial hair") to be cut by hair cutting device 1 is assumed to be "1.5432". Then, if the refractive index of surface 921 of human skin 92 is "1.4770", the condition that the refractive index of surface 921 of skin 92 is smaller than the refractive index of hair 91 is satisfied.

In short, in the present exemplary embodiment, as in the relationship of "light irradiator<skin<hair", the refractive index of surface 921 of skin 92 is larger than that of light irradiator 40 (core 41), and the refractive index of hair 91 is further larger than that of surface 921 of skin 92. That is, the refractive index of light irradiator 40 is smaller than the refractive index of hair 91 to be cut and smaller than the refractive index of surface 921 of skin 92.

As described above, in hair cutting device 1 according to the present exemplary embodiment, since the refractive index of light irradiator 40 is smaller than the refractive index of hair 91 to be cut, in a state where hair 91 is in contact with light irradiator 40, light leaks from light irradiator 40 to hair 91. Therefore, hair 91 is cut by energy of light leaking from light irradiator 40 to hair 91. The principle (mechanism) of cutting hair 91 will be described in detail in the section of "(2.5) Usage example". On the other hand, in a state where hair 91 is not in contact with light irradiator 40 and only air (refractive index: 1.0) is in contact with light irradiator 40, the amount of light leakage from light irradiator 40 can be suppressed to be small by the difference in refractive index between light irradiator 40 and the air.

Furthermore, as the relationship of the refractive index, it is more preferable that the difference between the refractive index of light irradiator 40 and the refractive index of hair 91 to be cut is as small as possible. That is, while the refractive indices of the three of surface 921 of skin 92, hair 91, and light irradiator 40 satisfy the above-described magnitude relationship, the differences are preferably as small as possible. As a result, the refractive index of light irradiator 40 becomes a value close to the refractive index of hair 91 to be cut, and in a state where hair 91 is in contact with light irradiator 40, light easily leaks from light irradiator 40 to hair 91.

In the present exemplary embodiment, as an example, the refractive index of light irradiator 40 (core 41) is "1.4698", the refractive index of surface 921 of skin 92 is "1.4770", and the refractive index of hair 91 is "1.5432", and it can be said that the refractive index of light irradiator 40 and the refractive index of surface 921 of skin 92 are almost the same. Here, "the refractive indices are almost the same" means that, in a case where there are two refractive indices different from each other, both have values close to each other to such an extent that the smaller refractive index is included within the range of ±5% of the larger refractive index. In this case, for example, when the incident angle of light (angle with the normal line of surface 921 of skin 92) is 80 degrees (incident NA is about 0.17), the reflectance (s polarized light) at the interface between an object having a refractive index of −5% of the refractive index of hair 91 and an object having a refractive index of that of hair 91 is 13.2%, the reflectance (s polarized light) at the interface between light irradiator 40 and hair 91 is 12.5%, and the reflectance (s polarized light) at the interface between skin 92 and hair 91 is 11.3%. Thus, even if the refractive index changes by −5%, the reflectance changes only by 2%. That is, in the present exemplary embodiment, since the refractive index (1.4698) of light irradiator 40 and the refractive index of surface 921 of skin 92 are in the range of ±5% of the refractive index (1.5432) of hair 91, they can be said to be almost the same.

As described in the section of "(2.1) Definition", the refractive index varies depending on the wavelength even for the same substance, but the above-described relationship of the refractive index is unchanged at least in the range of the wavelength of the light output from light source 21. That is, at least in the range of the wavelength of the light output from light source 21 (e.g., in the range from 400 nm to 700 nm, inclusive), the refractive index satisfies the relationship of "light irradiator<skin<hair".

Furthermore, since the refractive index of cladding 42 is smaller than the refractive index of core 41, which is light irradiator 40, when the above-described condition is satisfied, the refractive index of cladding 42 is the smallest among the refractive indices of the four of core 41, cladding 42, surface 921 of skin 92, and hair 91. That is, the relationship among the refractive indices of the four is "cladding<core<skin<hair".

In hair cutting device 1 according to the present exemplary embodiment, as described above, at least at the time of cutting hair 91, the power density of the light passing through optical waveguide 4 is more than or equal to 50 kW/cm$^2$. That is, in optical waveguide 4 including core 41 and cladding 42, since light passes through the inside of core 41, the light intensity per unit area (1 cm$^2$) in the cross section of core 41 is more than or equal to 50 kW. Here, the power density of the light passing through optical waveguide 4 is not necessarily more than or equal to 50 kW/cm$^2$ at all times, and only needs to be more than or equal to 50 kW/cm$^2$ at least at the time of cutting hair 91 (at the time of cutting hair 91).

In the present exemplary embodiment, as an example, the power density of the light passing through optical waveguide 4 at the time of cutting hair 91 is from 50 kW/cm$^2$ to 300 kW/cm$^2$, inclusive. The power density of the light passing through optical waveguide 4 at the time of cutting hair 91 is preferably more than or equal to 70 kW/cm$^2$, at which hair 91 can be cut, and more preferably more than or equal to 75 kW/cm$^2$. Furthermore, the power density of the light passing through optical waveguide 4 at the time of cutting hair 91 is more preferably more than or equal to 100 kW/cm$^2$ to cut hair 91 quickly (e.g., in about 0.1 s). Furthermore, the power density of the light passing through optical waveguide 4 at the time of cutting hair 91 is preferably less than or equal to 200 kW/cm$^2$ in consideration of the light output of a laser applicable as a consumer product, the fiber diameter, and the like. In the present exemplary embodiment, as an example, it is assumed that the initial value of the power density of the light passing through optical waveguide 4 at the time of cutting hair 91 is 100 kW/cm$^2$.

Although details will be described in the section of "(2.5) Usage example" and the section of "(3) Action", with this power density, it is easy for hair cutting device 1 to efficiently cut hair 91 with the light with which light irradiator 40 irradiates hair 91.

In the present exemplary embodiment, the power density of the light passing through optical waveguide 4 is variable. That is, hair cutting device 1 according to the present exemplary embodiment is configured such that the power density of the light passing through optical waveguide 4 is not fixed to the initial value, and the power density of the light passing through optical waveguide 4 is changeable. Here, in particular, the power density of the light passing through optical waveguide 4 at the time of cutting hair 91 is not fixed to the initial value (100 kW/cm$^2$) but is changeable from the initial value. The power density of the light passing through optical waveguide 4 at the time of cutting hair 91 is preferably variable in a range of more than or equal to 50 kW/cm$^2$. The power density of the light passing through optical waveguide 4 may change continuously, i.e., may change stepwise (discontinuously).

In the present exemplary embodiment, the power density of the light passing through optical waveguide 4 is adjusted by the output from light source 21. That is, hair cutting device 1 according to the present exemplary embodiment constitutes hair cutting system 10 together with light source 21, and the power density of the light passing through optical waveguide 4 is adjusted by adjusting the output from light source 21. The "adjust" as mentioned here includes both an aspect in which the power density is set to a predetermined value and an aspect in which the power density is changed as described above. In short, when the power density of the light passing through optical waveguide 4 is fixed to the initial value, the magnitude of the output from light source 21 is determined such that the power density becomes the initial value (100 kW/cm$^2$). On the other hand, when the power density of the light passing through optical waveguide 4 is changed from the initial value to a desired value, the magnitude of the output from light source 21 is determined such that the power density becomes a desired value after the change. The configuration for determining the magnitude of the output from light source 21 will be described in detail in the section of "(2.6) Control circuit".

(2.4) Holding Structure of Optical Waveguide

Next, details of the holding structure of optical waveguide 4 in hair cutting device 1 according to the present exemplary embodiment will be described with reference to FIGS. 2A and 2B.

As described above, hair cutting device 1 includes holding member 5 that holds optical waveguide 4. Here, as illustrated in FIGS. 2A and 2B, holding member 5 holds optical waveguide 4 in an aspect where light irradiator 40 is exposed from at least one face. That is, optical waveguide 4 is held by holding member 5 in an aspect where at least light irradiator 40 is exposed on a face of holding member 5 facing forward (negative orientation of the Y axis) in the traveling direction of hair cutting device 1. More specifically, entire core 41 constituting light irradiator 40 is not exposed but at least a face of core 41 facing forward (negative orientation of the Y axis) in the traveling direction of hair cutting device 1 is exposed from holding member 5. A region of core 41 exposed from holding member 5 in this manner functions as light irradiator 40 that irradiates hair 91 with light to cut hair 91.

Since holding member 5 is fixed to fixing block 32 of head 3 as described above, optical waveguide 4 (light irradiator 40) is indirectly fixed to second case 30 of head 3 via holding member 5 and fixing block 32.

Here, all of light irradiator 40 of optical waveguide 4, holding member 5, and fixing block 32 are exposed to the outside of second case 30 (see FIG. 1B) of head 3 through opening 31 (see FIG. 1B). Moreover, in opening 31, fixing block 32 and holding member 5 are disposed biasedly on the rear side (i.e., positive side of the Y axis) in the traveling direction of hair cutting device 1 (head 3) in the shorter direction (Y axis direction) of opening 31. Therefore, as viewed from holding member 5, a gap is secured between hair cutting device 1 and the peripheral edge of opening 31 on the front side (i.e., negative side of the Y axis) in the traveling direction of hair cutting device 1, and hair 91 to be cut can be taken into opening 31 through the gap. In other words, as illustrated in FIG. 2A, hair 91 to be cut can be introduced between a face of holding member 5 on which optical waveguide 4 is held such that light irradiator 40 is exposed, i.e., the face facing forward (negative orientation of the Y axis) in the traveling direction of hair cutting device 1, and the peripheral edge of opening 31.

With the above-described configuration, as illustrated in FIG. 2A, hair 91 to be cut is introduced into second case 30 from opening 31 to a position opposing light irradiator 40 held by holding member 5. In this state, a part of light irradiator 40 exposed from at least holding member 5 holding optional waveguide 4 (face facing the negative orientation of the Y axis) faces hair 91 to be cut. Thus, in optical waveguide 4, light irradiator 40 can be brought into contact with hair 91 to be cut.

In the present exemplary embodiment, holding member 5 includes base 51 and adhesive member 52. Adhesive member 52 bonds optical waveguide 4 to base 51. Base 51 and adhesive member 52 are both made of a synthetic resin having light transmissivity. In particular, base 51 is a resin molded product molded using a mold. On the other hand, adhesive member 52 is a cured product obtained by curing a paste resin that is an adhesive. That is, adhesive member 52 is a cured product of an adhesive for joining base 51 with optical waveguide 4.

Therefore, in order to achieve optical waveguide 4 in a state of being held by holding member 5, adhesive member 52 only needs to be cured by embedding a part of optical waveguide 4 into adhesive member 52, for example, in a state where paste adhesive member 52 is applied to base 51. As a result, holding member 5 can hold optical waveguide 4 in an aspect where light irradiator 40 is exposed from one face of holding member 5 by exposing a part of optical waveguide 4 from adhesive member 52 while bonding optical waveguide 4 to base 51 with adhesive member 52.

Base 51 is formed in a prismatic shape having a length along the X axis. Base 51 is fixed to fixing block 32 on a face facing forward (negative orientation of the Y axis) in the traveling direction of hair cutting device 1 by an appropriate means such as adhesion, welding, bonding, or coupling using a fastening member (screw or the like). In the present exemplary embodiment, the refractive index of base 51 is more than or equal to the refractive index of core 41 (light irradiator 40).

As illustrated in FIG. 2B, base 51 has four faces of opposing face 511, side face 512, back face 513, and rear face 514. The cross section orthogonal to the length (X axis) of base 51 has a substantially rectangular shape with these four faces as four sides. Opposing face 511 is a face opposing surface 921 of skin 92 at the time of cutting hair 91. Side face 512 is a face that intersects surface 921 of skin 92 at the time of cutting hair 91, and is a face adjacent to opposing face 511. Back face 513 is a face facing the opposite side of opposing face 511, and is a face adjacent to side face 512. Rear face 514 is a face facing the opposite side to side face 512 and, is a face adjacent to back face 513. That is, a face of base 51 facing the negative orientation of the Z axis is opposing face 511, and a face facing the negative orientation of the Y axis is side face 512. Furthermore, a face of base 51 facing the positive orientation of the Z axis is back face 513, and a face facing the positive orientation of the Y axis is rear face 514.

In the present exemplary embodiment, optical waveguide 4 is held on side face 512 of these opposing face 511, side face 512, back face 513, and rear face 514. That is, in the present exemplary embodiment, holding member 5 has side face 512 that intersects surface 921 of skin 92 at the time of cutting hair 91. Optical waveguide 4 is held by side face 512 of holding member 5. In particular, side face 512 is a face facing forward (negative orientation of the Y axis) in the traveling direction of hair cutting device 1 (head 3) of base 51. Therefore, light irradiator 40 of optical waveguide 4 is fixed to the face of holding member 5 facing forward (negative orientation of the Y axis) in the traveling direction of hair cutting device 1.

Adhesive member 52 bonds optical waveguide 4 to base 51. In the present exemplary embodiment, adhesive member 52 is provided on side face 512 of base 51 so that optical waveguide 4 is held on side face 512 of base 51, and adhesive member 52 joins base 51 with optical waveguide 4. Here, adhesive member 52 is disposed over the entire length in the longitudinal direction (X axis direction) of base 51. Therefore, optical waveguide 4 is bonded to base 51 by adhesive member 52 over the entire length in the longitudinal direction of base 51.

Since adhesive member 52 is a cured product of a paste resin as an adhesive, it is difficult to completely control the shape of adhesive member 52, but it is possible to control the shape of adhesive member 52 to some extent by, for example, the amount of adhesive member 52 provided on side face 512 of base 51. In the present exemplary embodiment, as illustrated in FIG. 2B, in the cross section orthogonal to the longitudinal direction (X axis direction) of base 51, the shape of adhesive member 52 is controlled such that a part of core 41 of optical waveguide 4 is buried in adhesive member 52 and a part of core 41 is exposed from adhesive member 52. More specifically, adhesive member 52 crawls up along the periphery of core 41 due to the "wettability" of core 41 to a height of substantially a half (i.e., radius) of core 41 in the traveling direction (Y axis direction) of hair cutting device 1. As a result, a half periphery of the periphery of core 41 of optical waveguide 4 is covered with adhesive member 52, and the remaining half periphery is exposed from holding member 5 (adhesive member 52) to constitute light irradiator 40.

In the present exemplary embodiment, the refractive index of adhesive member 52 is smaller than the refractive index of light irradiator 40. That is, if the refractive index of light irradiator 40 (core 41) is "1.4698", the refractive index of adhesive member 52 is smaller than "1.4698". This can appropriately restrict the amount of light leakage from core 41 to adhesive member 52, and can suppress a decrease in the power density of the light caused due to light leakage from core 41 more than necessary. In the present exemplary embodiment, since the region of optical waveguide 4 from which cladding 42 is removed and core 41 is exposed constitutes light irradiator 40, adhesive member 52 comes into direct contact with light irradiator 40 (core 41). Therefore, as an example, the refractive index of adhesive member 52 is equal to the refractive index of cladding 42 or less than or equal to the refractive index of cladding 42.

As described above, the arrangement of fixing block 32 and holding member 5 with respect to second case 30 is determined such that the face of each of fixing block 32 and holding member 5 facing the negative orientation of the Z axis is flush with the face of second case 30 facing the negative orientation of the Z axis. More specifically, the face of each of fixing block 32 and base 51 of holding member 5 facing the negative orientation of the Z axis is flush with the surface of second case 30 facing the negative orientation of the Z axis. The face of base 51 facing the negative orientation of the Z axis is opposing face 511. Therefore, in hair cutting device 1 (head 3), in a state where the surface of second case 30 facing the negative orientation of the Z axis is brought into contact with skin 92, fixing block 32 and base 51 of holding member 5 are also brought into contact with skin 92.

In the present exemplary embodiment, positioner 53 that positions optical waveguide 4 is formed on side face 512 of base 51 where optical waveguide 4 is held. Positioner 53 positions optical waveguide 4 at least in a plane orthogonal to the length of optical waveguide 4, i.e., in a Y-Z plane orthogonal to the X axis. As described above, in the present exemplary embodiment, holding member 5 includes positioner 53 that positions optical waveguide 4 in a plane orthogonal to the length of optical waveguide 4.

Here, as illustrated in FIG. 2B, positioner 53 includes a groove formed on side face 512 of base 51. That is, positioner 53 is a groove formed on one face (side face 512) of holding member 5. The groove as positioner 53 is formed over the entire length in the longitudinal direction (X axis direction) of base 51. Optical waveguide 4 is held on side face 512 of base 51 such that at least a part of core 41 exposed by removing cladding 42 is accommodated in the groove as positioner 53. That is, at least a part of optical waveguide 4 is accommodated in the groove (positioner 53).

Here, in the present exemplary embodiment, as an example, the groove as positioner 53 is a groove having a V-shaped cross section that becomes deeper toward the center in the shorter direction (width direction). As described above, by being disposed in the groove (positioner 53) having a shape that becomes deeper toward the center in the shorter direction (width direction), optical waveguide 4 is disposed substantially at the center in the shorter direction (width direction) of the groove as positioner 53 due to a self-alignment effect. In particular, in the configuration in which optical waveguide 4 is bonded to base 51 by adhesive member 52 as described in the present exemplary embodiment, there is a possibility that optical waveguide 4 is displaced before adhesive member 52 is cured. Therefore, it is useful to exhibit the self-alignment effect.

In the present exemplary embodiment, holding member 5 holds optical waveguide 4 such that a gap is generated between light irradiator 40 and base 51 at least at a time other than the time of cutting hair 91. That is, at least at a time other than the time of cutting hair 91, as illustrated in FIG. 2B, base 51 of holding member 5 and light irradiator 40 are not in contact with each other, and light irradiator 40 is held with a certain distance from base 51. Here, in the present exemplary embodiment, as described above, the refractive index of base 51 is more than or equal to the refractive index of core 41 (light irradiator 40). Therefore, if light irradiator 40 comes into contact with base 51, light leaks to base 51 from the contact region of light irradiator 40 with base 51, and the utilization efficiency of the light as hair cutting device 1 may be reduced. Therefore, in hair cutting device 1 according to the present exemplary embodiment, a decrease in light utilization efficiency is suppressed by separating light irradiator 40 from base 51.

In particular, in the present exemplary embodiment, a region of adhesive member 52 interposed between base 51 and optical waveguide 4 has thickness D1 more than or equal to the wavelength of the light passing through optical waveguide 4. Thickness D1 of the region of adhesive member 52 interposed between base 51 and optical waveguide 4 means the shortest distance between base 51 and optical waveguide 4 opposing each other across adhesive member 52 as illustrated in FIG. 2B. That is, since adhesive member 52 for bonding optical waveguide 4 to base 51 is interposed between light irradiator 40 (core 41) of optical waveguide 4 and base 51, a gap is secured between light irradiator 40 and base 51 by this adhesive member 52. However, when the thickness of adhesive member 52 interposed between base 51 and optical waveguide 4 is small (thin), light may leak to base 51 due to light (evanescent wave) seeping out to adhesive member 52 from the interface between optical waveguide 4 (core 41) and adhesive member 52. Such an evanescent wave is generated in a range of about one wavelength of light from the interface. Therefore, in the present exemplary embodiment, as illustrated in FIG. 2B, thickness D1 of adhesive member 52 interposed between base 51 and optical waveguide 4 is set to be more than or equal to the wavelength of the light passing through optical waveguide 4, so that the evanescent wave is less likely to affect base 51. As an example, when the wavelength of the light passing through optical waveguide 4, i.e., the wavelength of the light generated by light source 21 is 700 nm, thickness D1 of adhesive member 52 interposed between base 51 and optical waveguide 4 is more than or equal to 700 nm.

Furthermore, in the present exemplary embodiment, hair cutting device 1 has a contact surface that comes into contact with skin 92 at the time of cutting hair 91. Optical waveguide 4 is held by holding member 5 such that height L0 of light irradiator 40 from the contact surface is less than or equal to 100 μm. The "contact surface" referred to in the present disclosure means a face of hair cutting device 1 that comes into contact with skin 92 at the time of cutting hair 91, and is basically a face positioned in the most negative direction of the Z axis in hair cutting device 1. Here, hair cutting device 1 according to the present exemplary embodiment includes at least opposing face 511 of base 51 as a contact surface that comes into contact with skin 92. Furthermore, since the face of fixing block 32 facing the negative orientation of the Z axis and the face of second case 30 facing the negative orientation of the Z axis are opposing faces of base 51, these are also included in the contact surface. Height L0 of light irradiator 40 in the Z axis direction from the contact surface is equal to the height of light irradiator 40 from surface 921 of skin 92 at the time of cutting hair 91. That is, in the present exemplary embodiment, as illustrated in FIG. 2B, height L0 of light irradiator 40 from opposing face 511 that is the contact surface is set to less than or equal to 100 μm, so that the distance (height) from surface 921 of skin 92 to light irradiator 40 at the time of cutting hair 91 becomes less than or equal to 100 μm.

However, in the present exemplary embodiment, height L0 of light irradiator 40 from opposing face 511, which is the contact surface, is more than or equal to 1 μm, and is not zero (0). In other words, in hair cutting device 1, since light irradiator 40 has height L0 from the contact surface (opposing face 511) to some extent, light irradiator 40 can be separated from surface 921 of skin 92 at the time of cutting hair 91. Thus, since light irradiator 40 of optical waveguide 4 is separated from surface 921 of skin 92, for example, even if there is a bump such as an acne on surface 921 of skin 92, light irradiator 40 is less likely to be caught by the bump.

When holding member 5 includes positioner 53 as in the present exemplary embodiment, the height of positioner 53 from the contact surface may be defined instead of height L0 of light irradiator 40 from the contact surface. That is, the distance from the contact surface (opposing face 511 or the like) in the Z axis direction to the edge of the groove as positioner 53 is preferably less than or equal to 100 μm. In particular, in the present exemplary embodiment, the height of positioner 53 from the contact surface, i.e., the distance from the contact surface (opposing face 511 or the like) in the Z axis direction to the edge of the groove as positioner 53 is more than or equal to 1 μm.

(2.5) Usage Example

Next, a usage example of hair cutting device 1 and hair cutting system 10 according to the present exemplary embodiment will be described with reference to FIGS. 3A to 4B.

That is, in the present exemplary embodiment, hair cutting device 1 and hair cutting system 10 having the above-described configurations are used for cutting (here, "shaving") hair 91 (here, "facial hair"). At this time, the user brings head 3 of hair cutting system 10, i.e., the face of second case 30 facing the negative orientation of the Z axis into contact with skin 92 (of the face) of the user in a state where the user holds grip 2 of hair cutting system 10 with one hand to hold hair cutting system 10. As a result, as illustrated in FIG. 3A, hair 91 to be cut is introduced into second case 30 from opening 31 to a position opposing light irradiator 40 held by holding member 5.

As illustrated in FIG. 3A, in a state where light irradiator 40 is not in contact with hair 91, air comes into contact with light irradiator 40. Therefore, light leakage from light irradiator 40 hardly occurs due to a difference in refractive index between light irradiator 40 and air. In this state, the user moves head 3 (second case 30) as hair cutting device 1 in the direction of arrow A1 in FIG. 3A along surface 921 of skin 92.

As head 3 (second case 30) moves, as illustrated in FIG. 3B, light irradiator 40 comes into contact with hair 91 positioned forward (i.e., negative orientation of the Y axis) in the traveling direction of head 3. At this time, hair 91 is irradiated with light from light irradiator 40 such that the light leaks to hair 91 due to a difference in refractive index between light irradiator 40 and hair 91. That is, since the refractive index of light irradiator 40 is smaller than the refractive index of hair 91 to be cut, in a state where hair 91 is in contact with light irradiator 40, light leaks from light irradiator 40 to hair 91, and hair 91 is irradiated with light from light irradiator 40.

Furthermore, in the state illustrated in FIG. 3B, a part of the light with which light irradiator 40 irradiates hair 91 is scattered, so that skin 92 around hair 91 is also irradiated with the light from light irradiator 40. Specifically, a part of the light which has leaked from the contact region with hair 91 in light irradiator 40 is scattered by hair 91 to irradiate skin 92. As illustrated in FIG. 3B, let the light with which mainly hair 91 is irradiated be first irradiation light Op1, and light with which mainly skin 92 is irradiated be second irradiation light Op2. That is, in a state where hair 91 is in contact with light irradiator 40, light irradiator 40 irradiates hair 91 with first irradiation light Op1, and skin 92 is irradiated with second irradiation light Op2.

In particular, when hair 91 is irradiated with first irradiation light Op1 from light irradiator 40, hair 91 is cut by the energy of the light (first irradiation light Op1) with which light irradiator 40 irradiates hair 91. In short, in the present exemplary embodiment, the wavelength (e.g., from 400 nm to 700 nm, inclusive) of the light output from light source 21 and passing through optical waveguide 4 includes the wavelength of the light absorbed by the chromophore (part of a molecule that provides the molecule with its color) in hair 91. Therefore, first irradiation light Op1 is converted into heat by being absorbed by the chromophore of hair 91, and this heat breaks the bonds of the molecules of hair 91, or melts or burns hair 91. The chromophore that can be a target of the light (first irradiation light Op1) with which light irradiator 40 irradiates hair 91 includes, for example, a chromophore such as keratin or water.

As described above, the user can cut hair 91 protruding from skin 92 by moving head 3 (second case 30) as hair cutting device 1 in the orientation of arrow A1 (see FIG. 3A) along skin 92. Therefore, after optical waveguide 4 passes, only the root of uncut hair 91 remains on skin 92 as illustrated in FIG. 3C.

However, in hair cutting device 1, as illustrated in FIG. 3B, even if light irradiator 40 does not come into contact with hair 91, hair 91 may be irradiated with light (evanescent wave) seeping out to the air side from the interface between light irradiator 40 and the air, for example. Therefore, not only when light irradiator 40 comes into contact with hair 91, but also when light irradiator 40 and hair 91 come close to each other just before coming into contact, light irradiator 40 of hair cutting device 1 can sometimes cut hair 91 by irradiating hair 91 with first irradiation light Op1.

Figure 4B:
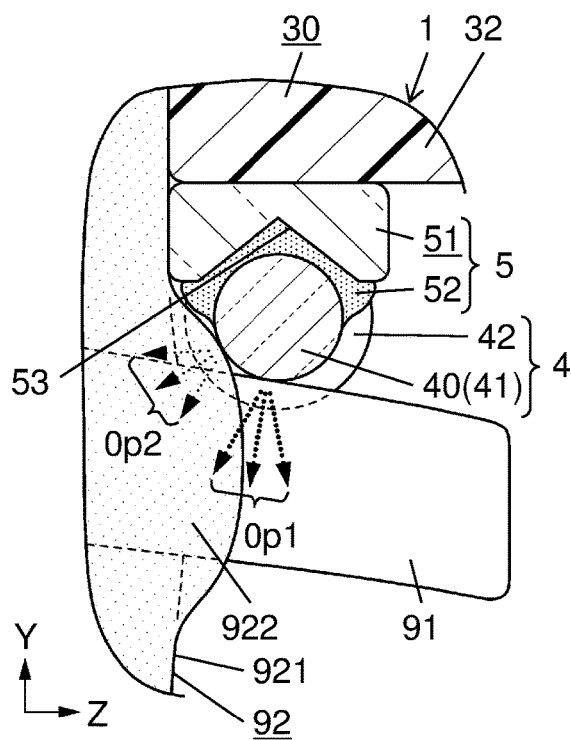
FIG. 4B is a schematic sectional view illustrating an operation of the hair cutting device at the time of cutting hair, particularly a scene of irradiating the hair with light.

Depending on the condition of skin 92, as illustrated in FIGS. 4A and 4B, when hair 91 (here, "facial hair") is cut (here, "shaved") using hair cutting device 1 and hair cutting system 10, light irradiator 40 may come into contact with a part of skin 92. FIGS. 4A and 4B illustrate use examples of hair cutting device 1 and hair cutting system 10 in a case where bump 922 such as an acne exists around hair 91 (around a hair root) on skin 92. Bump 922 is a region of skin 92 that is raised compared to surface 921 of skin 92 around bump 922.

That is, as illustrated in FIG. 4A, in a state where light irradiator 40 is not in contact with hair 91, air comes into contact with light irradiator 40. Therefore, light leakage from light irradiator 40 hardly occurs due to a difference in refractive index between light irradiator 40 and air. In this state, the user moves head 3 (second case 30) as hair cutting device 1 in the direction of arrow A1 in FIG. 4A along surface 921 of skin 92.

As head 3 (second case 30) moves, as illustrated in FIG. 4B, light irradiator 40 comes into contact with hair 91 positioned forward (i.e., negative orientation of the Y axis) in the traveling direction of head 3. At this time, hair 91 is irradiated with light (first irradiation light Op1) from light irradiator 40 such that the light leaks to hair 91 due to a difference in refractive index between light irradiator 40 and hair 91. When hair 91 is irradiated with first irradiation light Op1 from light irradiator 40, hair 91 is cut by the energy of the light (first irradiation light Op1) with which light irradiator 40 irradiates hair 91.

Furthermore, in the state illustrated in FIG. 4B, light irradiator 40 also comes into contact with bump 922 around hair 91 on skin 92. At this time, skin 92 is irradiated with light from light irradiator 40 such that the light leaks to skin 92 due to a difference in refractive index between light irradiator 40 and surface 921 (bump 922) of skin 92. That is, since the refractive index of light irradiator 40 is smaller than the refractive index of surface 921 of skin 92, in a state where skin 92 is in contact with light irradiator 40, light leaks from light irradiator 40 to skin 92, and light irradiator 40 irradiates skin 92 with light (second irradiation light Op2). At this time, light irradiator 40 directly irradiates skin 92 with second irradiation light Op2, and bump 922 is mainly irradiated with second irradiation light Op2.

(2.6) Control Circuit

Next, the configuration of control circuit 6 of hair cutting system 10 according to the present exemplary embodiment will be described with reference to FIGS. 5 and 6.

Figure 5:
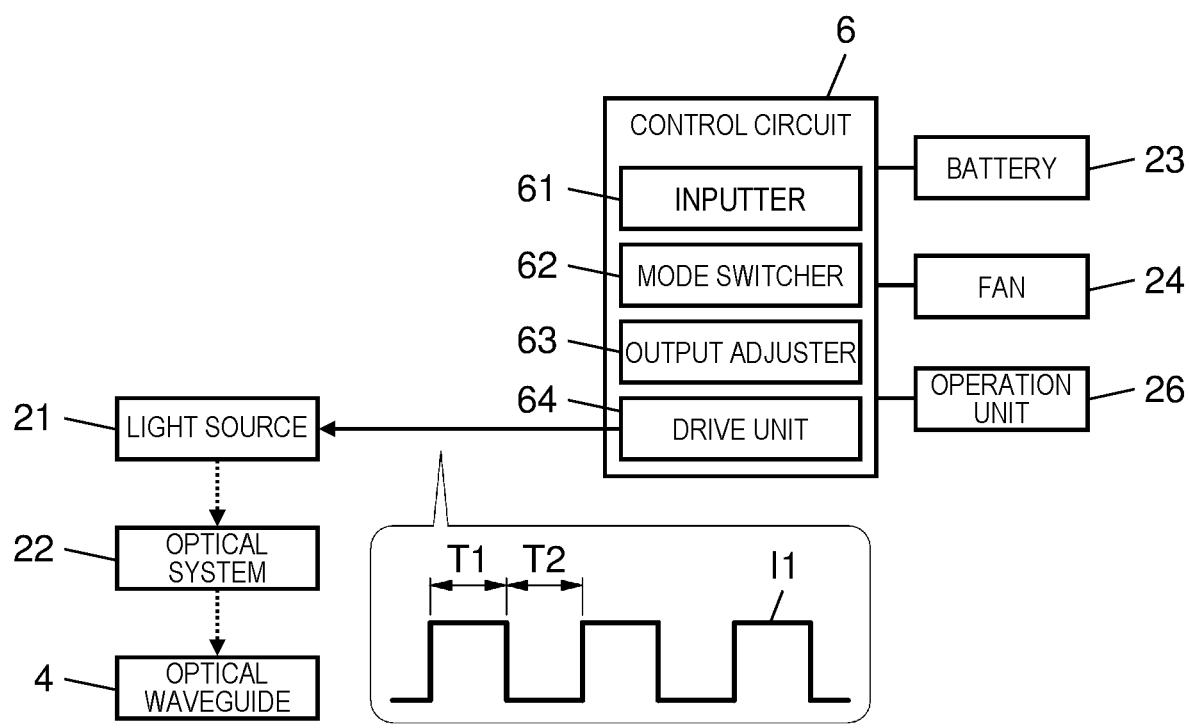
FIG. 5 is a block diagram illustrating a schematic configuration of a control circuit of the hair cutting system.
Figure 6:
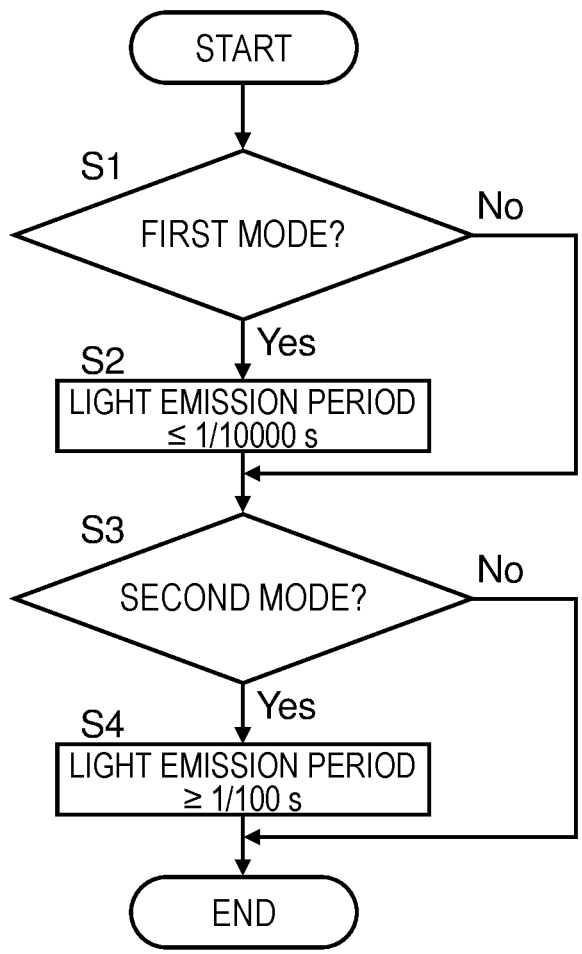
FIG. 6 is a flowchart illustrating an operation example of the hair cutting system.

As illustrated in FIG. 5, control circuit 6 is electrically connected to light source 21, battery 23, fan 24, operation unit 26, and the like. Control circuit 6 includes inputter 61, mode switcher 62, output adjuster 63, and drive unit 64.

Control circuit 6 includes, for example, a microcontroller having more than or equal to one processor and more than or equal to one memory. The microcontroller achieves a function as control circuit 6 by executing a program recorded in more than or equal to one memory with more than or equal to one processor. The program may be recorded in a memory in advance, may be provided by being recorded in a non-transitory recording medium such as a memory card, or may be provided through an electric communication line. In other words, the program is a program for causing more than or equal to one processor to function as control circuit 6.

An electric signal responsive to a user's operation is input to inputter 61 from operation unit 26. For example, when operation unit 26 receives an operation such as switching on or off of light source 21, an electric signal responsive to this operation is input to inputter 61.

Mode switcher 62 switches the operation mode of light source 21. In the present exemplary embodiment, as the operation mode of light source 21, there are two types of modes of a first mode and a second mode, both of which will be described later. Mode switcher 62 switches between the first mode and the second mode, for example, in accordance with the electrical signal from inputter 61.

Drive unit 64 drives light source 21 by supplying power to light source 21. That is, drive unit 64 supplies drive current I1 to light source 21 including a semiconductor laser to cause light source 21 to emit light (turn on). Here, when driving light source 21, as illustrated in FIG. 5, drive unit 64 supplies rectangular wave-shaped drive current I1 that alternately repeats light emission period T1 and light-off period T2 to light source 21, thereby causing light source 21 to emit light. That is, drive unit 64 supplies drive current I1 including the pulse current to light source 21, and in response to this, light source 21 intermittently generates (blinks) light.

That is, since light source 21 emits light in light emission period T1 of drive current I1 and light source 21 is turned off in light-off period T2 of drive current I1, light source 21 intermittently generates (blinks) light in accordance with the frequency of drive current I1. In short, light source 21 intermittently generates light by repeating light emission period T1 and light-off period T2. In the present exemplary embodiment, as an example, the duty (ratio of light emission period T1 to one cycle) of drive current I1 is assumed to be 50%. That is, the time length of light emission period T1 is equal to the time length of light-off period T2.

In the present exemplary embodiment, light source 21 has two types of operation modes of the first mode and the second mode.

The first mode is a mode in which the action on skin 92 is prioritized, and is a mode in which the time length of light emission period T1 is less than or equal to 1/10000 seconds. That is, when the operation mode of light source 21 is the first mode, the time length of light emission period T1 of light source 21 is less than or equal to 1/10000 seconds. In other words, in the first mode, drive unit 64 drives light source 21 with drive current I1 having a frequency of more than or equal to 5 kHz. Thus, the maximum time for which light source 21 continuously generates light becomes less than or equal to 1/10000 seconds. In the present exemplary embodiment, as an example, the time length of light emission period T1 of light source 21 when the operation mode of light source 21 is the first mode is 1/15000 seconds.

The second mode is a mode in which cutting of hair 91 is prioritized, and is a mode in which the time length of light emission period T1 is more than or equal to 1/100 seconds. That is, when the operation mode of light source 21 is the second mode, the time length of light emission period T1 of light source 21 is more than or equal to 1/100 seconds. In other words, in the second mode, drive unit 64 drives light source 21 with drive current I1 having a frequency of less than or equal to 50 Hz. Thus, the minimum time for which light source 21 continuously generates light becomes more than or equal to 1/100 seconds. In the present exemplary embodiment, as an example, the time length of light emission period T1 of light source 21 when the operation mode of light source 21 is the second mode is 1/80 seconds.

Here, control circuit 6 includes mode switcher 62 that switches between the first mode and the second mode. That is, in the present exemplary embodiment, the operation mode of light source 21 can be switched between the first mode in which the time length of light emission period T1 is less than or equal to 1/10000 seconds and the second mode in which the time length of light emission period T1 is more than or equal to 1/100 seconds.

Output adjuster 63 adjusts the output of light source 21 by controlling drive unit 64. The output of light source 21 to be adjusted by output adjuster 63 includes the light intensity (brightness), the wavelength of light, and the like generated by light source 21. Output adjuster 63 adjusts the output of light source 21 in accordance with an electric signal from inputter 61, for example.

In particular, in the present exemplary embodiment, as described above, the power density of the light passing through optical waveguide 4 is adjusted by the output from light source 21. Therefore, output adjuster 63 adjusts the power density of the light passing through optical waveguide 4 by adjusting the magnitude (power density) of the output of light source 21. Specifically, output adjuster 63 adjusts the power density of the light output from light source 21 to optical waveguide 4 by changing the magnitude of drive current I1 supplied from drive unit 64 to light source 21.

Furthermore, as described above, in the case where the power density of the light passing through optical waveguide 4 is variable, a change in the power density is achieved by output adjuster 63. That is, output adjuster 63 changes the power density of the light passing through optical waveguide 4 by changing the magnitude (power density) of the output of light source 21. Output adjuster 63 changes the magnitude (power density) of the output of light source 21 in accordance with the electric signal from inputter 61, for example.

Next, an operation example of hair cutting system 10 including control circuit 6 described above will be described with reference to FIG. 6. FIG. 6 is a flowchart illustrating an operation example of hair cutting system 10 according to the present exemplary embodiment.

Hair cutting system 10 first determines whether or not the operation mode of light source 21 is the first mode (S1). At this time, if the operation mode is the first mode (S1: Yes), hair cutting system 10 sets the time length of light emission period T1 to less than or equal to 1/10000 seconds and drives light source 21 with drive unit 64 (S2). On the other hand, if the operation mode is not the first mode (S1: No), hair cutting system 10 skips process S2 and proceeds to process S3.

In process S3, hair cutting system 10 determines whether or not the operation mode of light source 21 is the second mode. At this time, if the operation mode is the second mode (S3: Yes), hair cutting system 10 sets the time length of light emission period T1 to more than or equal to 1/100 seconds and drives light source 21 with drive unit 64 (S4). On the other hand, if the operation mode is not the second mode (S3: No), hair cutting system 10 skips process S4 and ends the process.

Hair cutting system 10 repeatedly executes processes S1 to S4. The flowchart illustrated in FIG. 6 is merely an example of the operation of hair cutting system 10, and for example, the order of the processes may be appropriately changed, or the process may be appropriately added or omitted.

(3) Action

Next, expected actions of hair cutting device 1 and hair cutting system 10 according to the present exemplary embodiment will be described.

First, cutting of hair 91, which is a basic function of hair cutting device 1 and hair cutting system 10, is achieved by the mechanism described in the section of "(2.5) Usage example".

Here, in the present exemplary embodiment, since first irradiation light Op1 with which light irradiator 40 irradiates hair 91 has a wavelength of from 400 nm to 700 nm, inclusive, for example, first irradiation light Op1 is easily absorbed by the chromophore included in hair 91 such as keratin and water. Furthermore, in the present exemplary embodiment, at least at the time of cutting hair 91, the power density of the light passing through optical waveguide 4 is more than or equal to 50 kW/cm$^2$. Therefore, first irradiation light Op1 with which light irradiator 40 irradiates hair 91 can also have a power density (more than or equal to 50 kW/cm$^2$) sufficient for cutting hair 91.

In addition, in the present exemplary embodiment, as described above, when the operation mode of light source 21 is the second mode in which cutting of hair 91 is prioritized, the time length of light emission period T1 of light source 21 becomes more than or equal to 1/100 seconds. Therefore, for example, in one light emission period T1, hair cutting device 1 can irradiate hair 91 with first irradiation light Op1 having sufficient energy to cut hair 91. Therefore, according to hair cutting device 1 and hair cutting system 10 of the present exemplary embodiment, hair 91 can be cut in a relatively short time. Therefore, according to hair cutting device 1 and hair cutting system 10 of the present exemplary embodiment, hair 91 is less likely to be entangled or caught, and smooth cutting of hair 91 is easily achieved.

Furthermore, since hair cutting device 1 and hair cutting system 10 can cut hair 91 in a relatively short time. Therefore, hair cutting device 1 is less likely to stay at one location, and the same location of skin 92 is less likely to be irradiated with light for a long time. Therefore, skin 92 is less likely to be damaged. As a result, there is an advantage of providing improved hair cutting device 1 and hair cutting system 10.

Next, an action on skin 92, which is a secondary function of hair cutting device 1 according to the present exemplary embodiment, will be described.

That is, since second irradiation light Op2 with which light irradiator 40 irradiates skin 92 has a wavelength of from 400 nm to 700 nm, inclusive, an action on skin 92 such as sterilization or activation can also be expected. That is, when second irradiation light Op2 with which skin 92 is irradiated has a wavelength in the range from 400 nm to 450 nm, inclusive, for example, it can be expected to have a sterilizing action on propionibacterium acnes and the like existing on skin 92. In particular, as illustrated in FIGS. 4A and 4B, when bump 922 such as acne exists around hair 91 in skin 92, light irradiator 40 directly irradiates bump 922 with second irradiation light Op2, and more effective sterilization action and the like can be expected.

Furthermore, in a case where second irradiation light Op2 with which skin 92 is irradiated has a wavelength of, for example, from 450 nm to 700 nm, inclusive, an activation action of skin 92 can be expected. That is, when skin 92 is irradiated with second irradiation light Op2, skin 92 is activated, and an action such as so-called "skin beautifying effect", which includes improvement of skin quality, can be expected.

Furthermore, in the present exemplary embodiment, at least at the time of cutting hair 91, the power density of the light passing through optical waveguide 4 is more than or equal to 50 kW/cm$^2$. Therefore, second irradiation light Op2 with which light irradiator 40 irradiates skin 92 can also have the same power density (more than or equal to 50 kW/cm$^2$) as that of the light passing through optical waveguide 4. Here, in the present exemplary embodiment, height L0 of light irradiator 40 from opposing face 511, which is the contact surface, is more than or equal to 1 μm, and light irradiator 40 can be separated from surface 921 of skin 92 at the time of cutting hair 91. Therefore, basically, skin 92 is irradiated with second irradiation light Op2 scattered by hair 91, and the power density of second irradiation light Op2 with which skin 92 is irradiated can be appropriately suppressed to be small. On the other hand, since height L0 of light irradiator 40 from opposing face 511, which is the contact surface, is set to less than or equal to 100 μm, second irradiation light Op2 can also be effectively caused to act on bump 922 such as acne.

In addition, in the present exemplary embodiment, as described above, when the operation mode of light source 21 is the first mode in which the action on skin 92 is prioritized, the time length of light emission period T1 of light source 21 becomes less than or equal to 1/10000 seconds. Therefore, hair cutting device 1 can appropriately suppress the energy of second irradiation light Op2 with which skin 92 is irradiated to be small in one light emission period T1, for example. Specifically, assuming that the power density of the light passing through optical waveguide 4 is 50 kW/cm$^2$ and that the time length of one light emission period T1 is 1/10000 seconds, the energy of second irradiation light Op2 per unit area is suppressed to 5 J/cm$^2$ at the maximum.

Therefore, according to hair cutting device 1 and hair cutting system 10 of the present exemplary embodiment, not only cutting of hair 91 but also a secondary function such as an action on skin 92 can be expected. Moreover, in hair cutting device 1 and hair cutting system 10, by appropriately adjusting the energy of second irradiation light Op2 with which skin 92 is irradiated, it is possible to expect an action such as sterilization or activation of skin 92 while making it difficult to damage skin 92. As a result, there is an advantage of providing improved hair cutting device 1 and hair cutting system 10.

(4) Modifications

The first exemplary embodiment is merely one of various exemplary embodiments of the present disclosure. The first exemplary embodiment can be variously changed in accordance with design and the like, as long as the object of the present disclosure can be achieved. The drawings referred to in the present disclosure are all schematic drawings, and the ratio of each of the size and the thickness of each component in the drawings does not necessarily reflect the actual dimensional ratio. Hereinafter, modifications of the first exemplary embodiment will be listed. The modifications described below can be applied in appropriate combination.

(4.1) First Modification

Hair cutting device 1 according to a first modification of the first exemplary embodiment will be described with reference to FIGS. 7A to 8D.

Figure 7A:
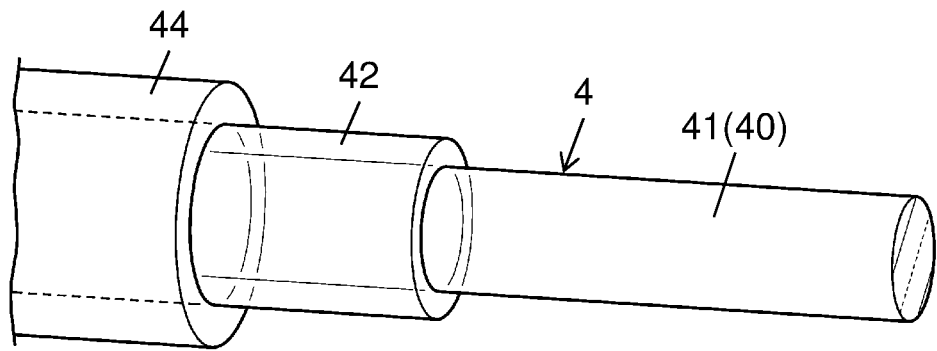
FIG. 7A is a schematic perspective view of an optical waveguide which is used in the hair cutting device.

In the present modification, the configuration of optical waveguide 4 is different from that of hair cutting device 1 according to the first exemplary embodiment. That is, in the first exemplary embodiment, as illustrated in FIG. 7A, in optical waveguide 4 including core 41 and cladding 42, cladding 42 is removed for a predetermined length from the tip end side and core 41 is exposed, so that exposed core 41 constitutes light irradiator 40. On the other hand, in the modification illustrated in FIG. 7B, in optical waveguide 4A, core 41 is exposed by removing only a part of cladding 42 in the circumferential direction of core 41 for a predetermined length from the tip end side. In the modification illustrated in FIG. 7C, optical waveguide 4B includes core 41 eccentric to cladding 42, and only a part of core 41 in the circumferential direction is exposed from cladding 42.

Figure 7B:
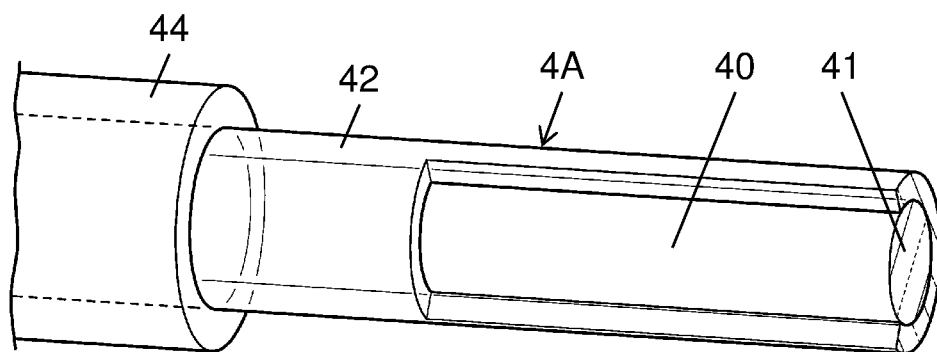
FIG. 7B is a schematic perspective view illustrating an example of an optical waveguide which is used in the hair cutting device according to a first modification of the first exemplary embodiment.
Figure 7C:
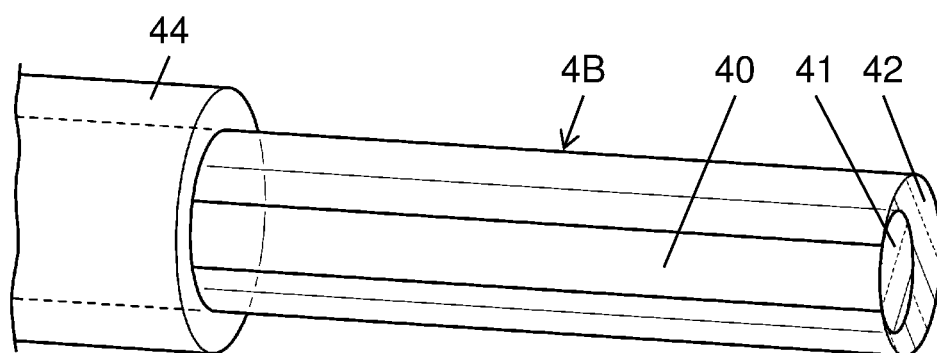
FIG. 7C is a schematic perspective view illustrating another example of the optical waveguide which is used in the hair cutting device according to the first modification of the first exemplary embodiment.

That is, in the modifications illustrated in FIGS. 7B and 7C, optical waveguides 4A and 4B each include cladding 42 that covers at least a part of core 41. Light irradiator 40 is formed of a part of core 41 in the circumferential direction and includes a region exposed from cladding 42. As described above, in the present modification, unlike the first exemplary embodiment in which cladding 42 does not exist over the entire circumference of core 41 in the circumferential direction, cladding 42 does not exist only in a part of core 41 in the circumferential direction. Therefore, in optical waveguides 4A and 4B in the present modification, a region of core 41 other than light irradiator 40 in the circumferential direction is covered with cladding 42, and thus, leakage of light more than necessary from core 41 hardly occurs.

Figure 8A:
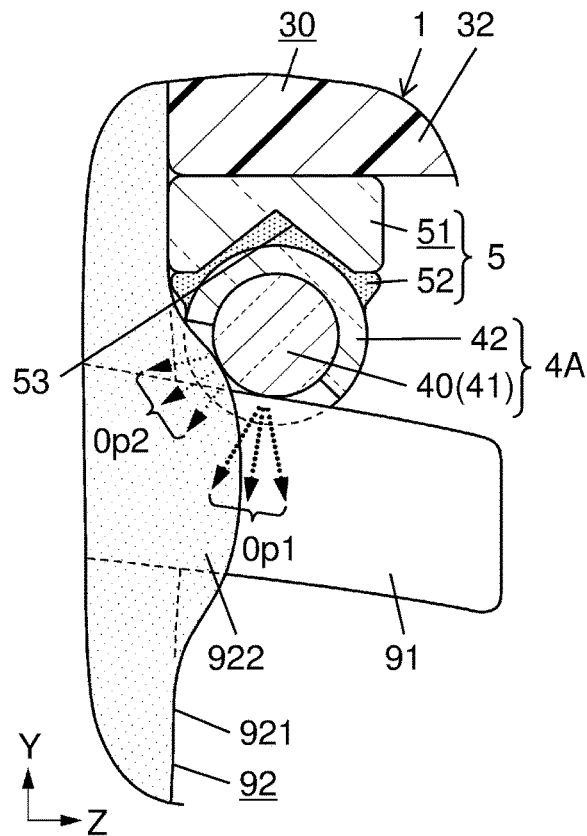
FIG. 8A is a schematic sectional view illustrating an example of a main part of the hair cutting device according to the first modification of the first exemplary embodiment.

FIG. 8A is a schematic sectional view illustrating hair cutting device 1 in a case where optical waveguide 4A illustrated in FIG. 7B is adopted instead of optical waveguide 4 on the basis of the configuration of hair cutting device 1 according to the first exemplary embodiment. Also in the modification illustrated in FIG. 8A, similarly to hair cutting device 1 according to the first exemplary embodiment, holding member 5 holds optical waveguide 4A in such an aspect where light irradiator 40 is exposed from at least one face. Even with such a configuration, light irradiator 40 of optical waveguide 4A irradiates hair 91 with first irradiation light Op1 and skin 92 is irradiated with second irradiation light Op2.

Figure 8B:
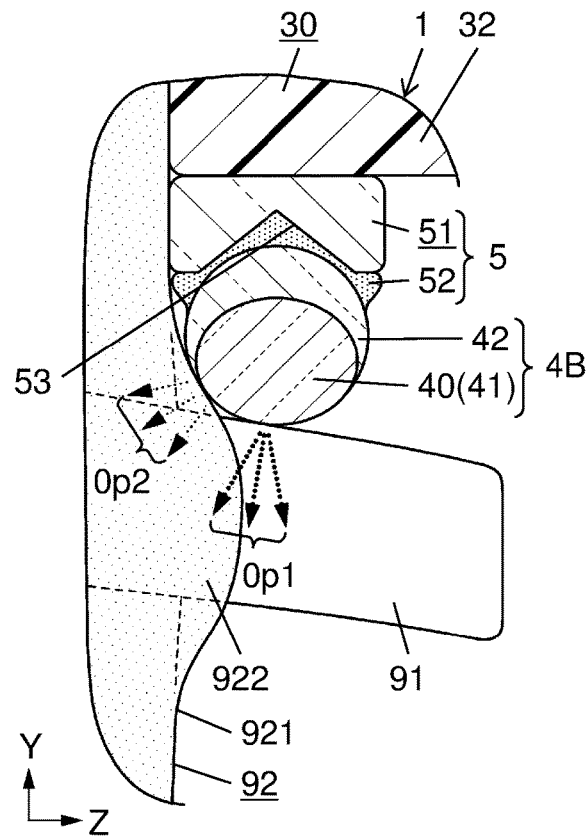
FIG. 8B is a schematic sectional view illustrating another example of the main part of the hair cutting device according to the first modification of the first exemplary embodiment.

FIG. 8B is a schematic sectional view illustrating hair cutting device 1 in a case where optical waveguide 4B illustrated in FIG. 7C is adopted instead of optical waveguide 4 on the basis of the configuration of hair cutting device 1 according to the first exemplary embodiment. Also in the modification illustrated in FIG. 8B, similarly to hair cutting device 1 according to the first exemplary embodiment, holding member 5 holds optical waveguide 4B in such an aspect where light irradiator 40 is exposed from at least one face. Even with such a configuration, light irradiator 40 of optical waveguide 4B irradiates hair 91 with first irradiation light Op1 and skin 92 is irradiated with second irradiation light Op2.

Figure 8C:
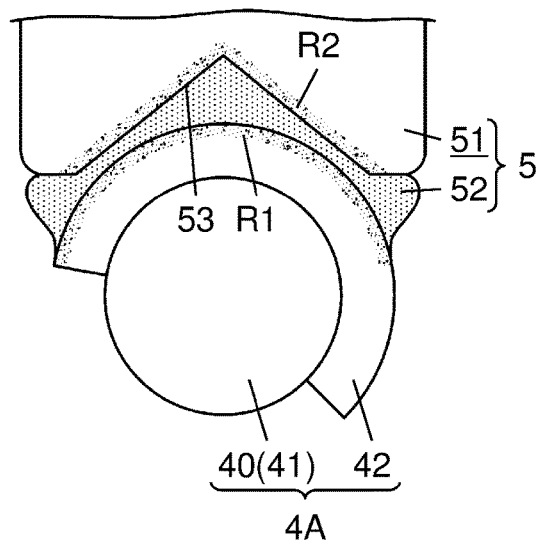
FIG. 8C is a schematic view illustrating a holding structure with a holding member of the optical waveguide in FIG. 8A.
Figure 8D:
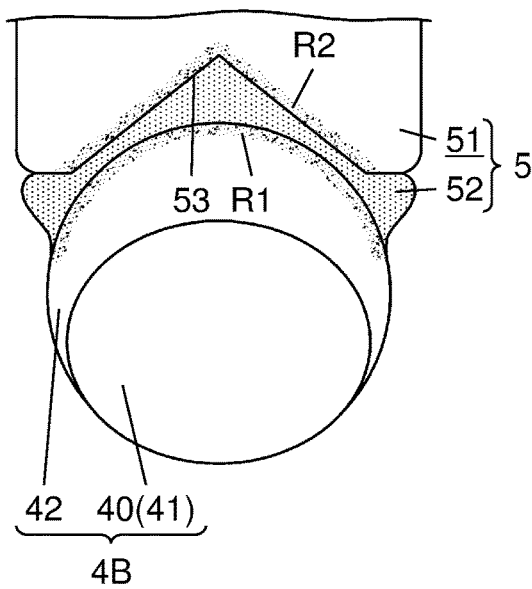
FIG. 8D is a schematic view illustrating the holding structure with the holding member of the optical waveguide in FIG. 8B.

As illustrated in FIGS. 8C and 8D, a region that comes into contact with adhesive member 52 at least at one of base 51 and optical waveguides 4A and 4B preferably has uneven surfaces R1 and R2 including at least one of a plurality of recesses and a plurality of projections. FIG. 8C is a schematic view illustrating the holding structure with holding member 5 of optical waveguide 4A in FIG. 8A, and FIG. 8D is a schematic view illustrating the holding structure with holding member 5 of optical waveguide 4B in FIG. 8B. In FIGS. 8C and 8D, ranges (regions) in which uneven surfaces R1 and R2 are formed are shaded (dot-hatched). That is, the shades representing uneven surfaces R1 and R2 are merely provided for the sake of convenience only to represent the ranges of uneven surfaces R1 and R2, and the shades are not applied to actual hair cutting device 1.

In the example of FIG. 8C, the region of base 51 in contact with adhesive member 52 has uneven surface R2, and the region of optical waveguide 4A in contact with adhesive member 52 has uneven surface R1. In the example of FIG. 8C, uneven surface R2 is formed on an inner periphery of a groove formed on side face 512 of base 51 as positioner 53, and uneven surface R1 is formed on an outer periphery of cladding 42 of optical waveguide 4A. More specifically, uneven surface R1 is formed on the outer periphery of cladding 42 of optical waveguide 4A, the outer periphery facing the opposite side (positive orientation of the Y axis) to light irradiator 40.

Similarly, in the example of FIG. 8D, the region of base 51 in contact with adhesive member 52 has uneven surface R2, and the region of optical waveguide 4B in contact with adhesive member 52 has uneven surface R1. In the example of FIG. 8D, uneven surface R2 is formed on an inner periphery of a groove formed on side face 512 of base 51 as positioner 53, and uneven surface R1 is formed on an outer periphery of cladding 42 of optical waveguide 4B. More specifically, uneven surface R1 is formed on the outer periphery of cladding 42 of optical waveguide 4A, the outer periphery facing the opposite side (positive orientation of the Y axis) to light irradiator 40.

The "uneven surface" referred to in the present disclosure means a face including at least one of a plurality of recesses and a plurality of projections. That is, uneven surfaces R1 and R2 may include only a plurality of recesses or may include only a plurality of projections. Furthermore, uneven surfaces R1 and R2 may include a plurality of recesses and one project. In this case, as an example, uneven surfaces R1 and R2 include one shaded projection and a plurality of recesses including a shaded region surrounded by this protrusion. Similarly, as an example, uneven surfaces R1 and R2 may include one shaded recess and a plurality of projections including a shaded region surrounded by this recess.

Here, as an example, uneven surfaces R1 and R2 include a plurality of recesses and a plurality of projections. The plurality of recesses and the plurality of projections on uneven surfaces R1 and R2 have an significantly small size that cannot be individually identified with the naked eye, and each of uneven surfaces R1 and R2 includes a large number of recesses and a large number of projections. That is, the recess and the projection are finer than the entire uneven surfaces R1 and R2. As a result, when a person sees uneven surfaces R1 and R2, uneven surfaces R1 and R2 look like a rough "satin" due to the presence of the recess and the projection. Uneven surfaces R1 and R2 including a large number of fine recesses and projections are formed by embossing, for example.

Such uneven surfaces R1 and R2 are formed of a large number of recesses and projections, and have a pattern (irregularity shape) such as a satin, a wrinkle pattern (emboss), a wood grain, a rock grain, a sand grain, or a geometric pattern as a whole.

The size of such fine recesses and projections can be expressed by the surface roughness of uneven surfaces R1 and R2, i.e., the shape of the recesses and projections is reflected on the roughness curve among the contour curves of uneven surfaces R1 and R2. Therefore, the size of the recesses and projections on uneven surfaces R1 and R2 corresponds to calculated average roughness (Ra) of uneven surfaces R1 and R2. Therefore, calculated average roughness (Ra) of the inner periphery (uneven surface R2) of the groove (positioner 53) is larger than calculated average roughness (Ra) of a region other than the groove (positioner 53) in side face 512 of base 51. In other words, the region of base 51 that comes into contact with adhesive member 52 is a face that is rougher than the region of base 51 that does not come into contact with adhesive member 52. Similarly, calculated average roughness (Ra) of the outer periphery (uneven surface R1) of cladding 42 is larger than calculated average roughness (Ra) of the outer periphery of core 41. In other words, the regions of optical waveguides 4A and 4B that come into contact with adhesive member 52 are faces that are rougher than the regions of optical waveguides 4A and 4B that do not come into contact with adhesive member 52.

Uneven surfaces R1 of optical waveguides 4A and 4B may be achieved by a layer of an inorganic member or an organic member including at least one of a plurality of recesses and a plurality of projections formed on the outer periphery of cladding 42. Alternatively, uneven surfaces R1 of optical waveguides 4A and 4B may be achieved by a layer of an inorganic member or an organic member including at least one of a plurality of recesses and a plurality of projections formed on the outer periphery of core 41.

Thus, since the region of at least one of base 51 and optical waveguides 4A and 4B that comes into contact with adhesive member 52 has uneven surfaces R1 and R2, the adhesive power (adhesion) of adhesive member 52 between base 51 and optical waveguides 4A and 4B is improved by the anchor effect. As a result, it is easy to improve the durability of the holding structure of optical waveguides 4A and 4B with holding member 5. Here, an example has been described in which the regions of both base 51 and optical waveguides 4A and 4B that come into contact with adhesive member 52 have uneven surfaces R1 and R2, but the region of only one of base 51 and optical waveguides 4A and 4B that comes into contact with adhesive member 52 may have an uneven surface. Furthermore, even in an aspect other than the first modification (e.g., the first exemplary embodiment or a modification other than the first modification of the first exemplary embodiment), it is possible to adopt a configuration in which a region of at least one of base 51 and optical waveguide 4 that comes into contact with adhesive member 52 has an uneven surface.

As in hair cutting device 1 according to the first modification, when a part of light irradiator 40 (core 41) is exposed from cladding 42, adhesive member 52 only needs to bond cladding 42 with base 51, and does not come into direct contact with light irradiator 40 (core 41). Therefore, the refractive index of adhesive member 52 does not need to be equal to the refractive index of cladding 42 or equal to or less than the refractive index of cladding 42, and can be appropriately set regardless of the refractive index of cladding 42.

(4.2) Second Modification

Hair cutting device 1 according to a second modification of the first exemplary embodiment will be described with reference to FIGS. 9A to 9F. As illustrated in FIGS. 9A to 9F, the present modification is different from the first exemplary embodiment in the aspect of holding core 41 (light irradiator 40) of optical waveguide 4 by holding member 5.

Figure 9A:
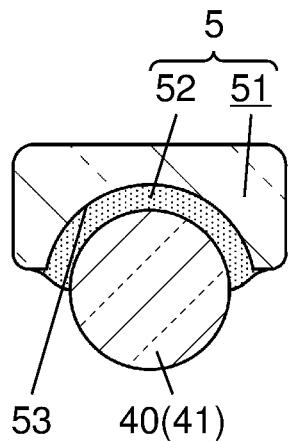
FIG. 9A is a schematic sectional view of a main part of a hair cutting device according to a second modification of the first exemplary embodiment.
Figure 9B:
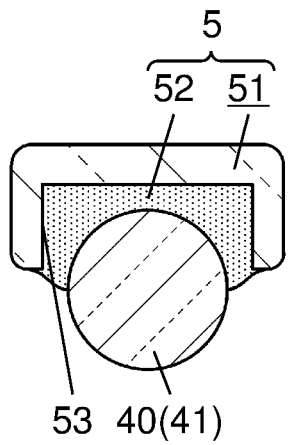
FIG. 9B is a schematic sectional view of the main part of the hair cutting device according to the second modification of the first exemplary embodiment.
Figure 9C:
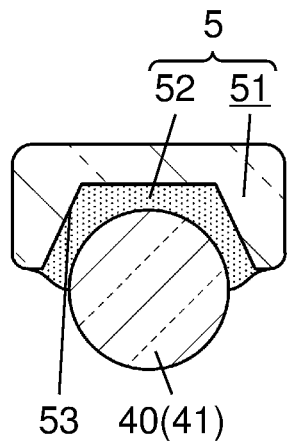
FIG. 9C is a schematic sectional view of the main part of the hair cutting device according to the second modification of the first exemplary embodiment.

In the examples illustrated in FIGS. 9A to 9C, the shape of the groove as positioner 53 formed on base 51 of holding member 5 is different from that of the first exemplary embodiment (V-shaped cross section). That is, in the example of FIG. 9A, the groove as positioner 53 is a groove having a semicircular arc (U-shaped) cross section that becomes deeper toward the center in the shorter direction (width direction). In the example of FIG. 9B, the groove as positioner 53 is a groove having a rectangular cross section with a uniform depth in the shorter direction (width direction). In the example of FIG. 9C, the groove as positioner 53 is a groove having a trapezoidal cross section that becomes deeper toward the center in the shorter direction (width direction).

Figure 9D:
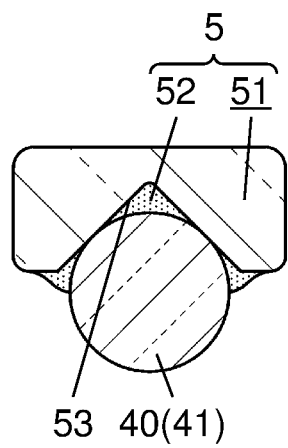
FIG. 9D is a schematic sectional view of the main part of the hair cutting device according to the second modification of the first exemplary embodiment.
Figure 9E:
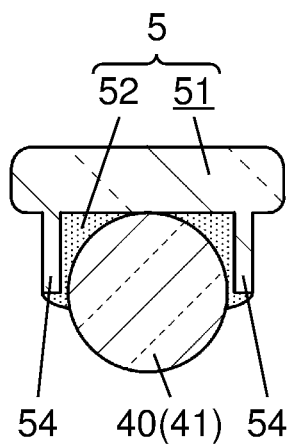
FIG. 9E is a schematic sectional view of the main part of the hair cutting device according to the second modification of the first exemplary embodiment.
Figure 9F:
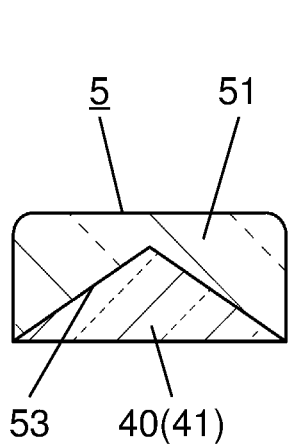
FIG. 9F is a schematic sectional view of the main part of the hair cutting device according to the second modification of the first exemplary embodiment.

In the examples illustrated in FIGS. 9D to 9F, holding member 5 holds optical waveguide 4 in a state where light irradiator 40 (core 41) is in contact with base 51. That is, in the example of FIG. 9D, core 41 is disposed in a groove having a V-shaped cross section as positioner 53 in a state where core 41 is in contact with the bottom face of positioner 53 (groove). In the example of FIG. 9E, positioner 54 is a rib protruding from both ends in the shorter direction on side face 512 (see FIG. 2B) of base 51, and core 41 is disposed between a pair of ribs, which is positioner 54. In the example of FIG. 9F, core 41 is disposed in a groove having a V-shaped cross section as positioner 53 so that core 41 fills positioner 53 (groove).

As clear from the example of FIG. 9F, inclusion of adhesive member 52 (see FIG. 2A and the like) in holding member 5 is not an essential configuration of hair cutting device 1. That is, even if holding member 5 does not have adhesive member 52, holding member 5 can hold optical waveguide 4, particularly core 41 as light irradiator 40. That is, even when holding member 5 has only base 51, light irradiator 40 of optical waveguide 4 can be held by holding member 5 (base 51). In this case, light irradiator 40 (core 41) only needs to be directly fixed to holding member 5 (base 51). Examples of the means for directly fixing core 41 to base 51 include a means for integrally molding core 41 and base 51 by two-color molding or the like, a means for welding core 41 to base 51, and a means for pressure-bonding core 41 to base 51.

(4.3) Other Modifications

Hereinafter, modifications of the first exemplary embodiment other than the first modification and the second modification will be described.

A function similar to that of control circuit 6 of hair cutting system 10 according to the first exemplary embodiment may be embodied by a control method, a computer program, or a recording medium in which the computer program has been recorded. That is, the function corresponding to control circuit 6 may be embodied by a control method, a computer program, a recording medium in which the computer program has been recorded, or the like.

Hair cutting system 10 in the present disclosure includes a computer system in control circuit 6 and the like. The computer system mainly includes a processor and a memory as hardware. When a processor executes a program recorded in the memory of the computer system, a function as control circuit 6 in the present disclosure is implemented. The program may be recorded in advance in the memory of the computer system, may be provided through a telecommunication line, or may be provided by being recorded in a non-transitory recording medium readable by the computer system, such as a memory card, an optical disk, and a hard disk drive. The processor of the computer system includes one or a plurality of electronic circuits including a semiconductor integrated circuit (IC) or a large-scale integration (LSI). The integrated circuit such as the IC or LSI mentioned here is called differently depending on the degree of integration, and includes integrated circuits called a system LSI, a very large scale integration (VLSI), or an ultra large scale integration (ULSI).

Furthermore, a field-programmable gate array (FPGA) programmed after manufacturing of the LSI, or a logic device that can reconfigure a joining relationship inside the LSI or reconfigure a circuit section inside the LSI can also be adopted as the processor. The plurality of electronic circuits may be aggregated into one chip or may be provided dispersedly on a plurality of chips. The plurality of chips may be aggregated into one device or may be provided dispersedly on a plurality of devices. The computer system mentioned here includes a microcontroller having more than or equal to one processor and more than or equal to one memory. Therefore, the microcontroller also includes one or a plurality of electronic circuits including a semiconductor integrated circuit or a large-scale integrated circuit.

It is not an essential configuration for hair cutting system 10 that at least some functions of hair cutting system 10 are aggregated into one housing, and the components of hair cutting system 10 may be provided dispersedly in a plurality of housings. At least some of functions of control circuit 6 and the like in hair cutting system 10 may be achieved by, for example, a server or a cloud (cloud computing).

On the other hand, in the first exemplary embodiment, at least some functions of hair cutting system 10 dispersed in a plurality of housings (cases) may be aggregated into one housing (case). For example, hair cutting system 10 may include an inseparable integrated case instead of first case 20 and second case 30. In this case, the components of hair cutting system 10 are accommodated into or attached to one case.

Operation unit 26 is not limited to a mechanical switch, and may be a touch switch, an optical or capacitance non-contact switch, a gesture sensor, or the like. Furthermore, operation unit 26 may be, for example, a communicator that receives an operation signal from an external terminal such as a smartphone, a voice inputter that receives a voice operation of the user, or the like.

Hair cutting device 1 may be combined with a shaver (including an electric shaver in which a blade is driven) that cuts hair 91 with a physical "blade". In this case, hair cutting device 1 includes a physical "blade" in addition to light irradiator 40, so that hair cutting device 1 can cut hair 91 with both the light irradiated from light irradiator 40 and the physical "blade".

Optical waveguide 4 is not limited to an optical fiber in which core 41 and cladding 42 are made of synthetic quartz, and may be, for example, an optical fiber made of quartz ($SiO_2$) or plastic. Examples of the plastic optical fiber include an optical fiber in which cladding 42 is made of a fluorine-based polymer or the like, and core 41 is made of a fully fluorinated polymer, polymethylmethacrylate, polycarbonate, or the like. Furthermore, optical waveguide 4 may be a slab waveguide, a rectangular optical waveguide, a photonic crystal fiber, or the like.

Optical waveguide 4 only needs to have core 41 as a minimum configuration, and cladding 42 may be appropriately omitted.

It is not an essential configuration to hair cutting device 1 that the refractive index of adhesive member 52 in holding member 5 is smaller than the refractive index of light irradiator 40. That is, the refractive index of adhesive member 52 may be more than or equal to the refractive index of light irradiator 40.

It is not an essential configuration to hair cutting device 1 that in holding member 5, optical waveguide 4 is bonded to base 51 with adhesive member 52 over the entire length in the longitudinal direction (X axis direction) of base 51. That is, holding member 5 may be configured to hold optical waveguide 4 by locally bonding optical waveguide 4 to base 51 with adhesive member 52 only in a part of base 51 in the longitudinal direction. In this case, optical waveguide 4 has a region bonded to base 51 and a region not bonded to base 51. In this case, it is preferable that adhesive member 52 bonds optical waveguide 4 to base 51 at a plurality of places so as to suppress the deviation of optical waveguide 4 and the like as much as possible.

The gap between light irradiator 40 and base 51 only needs to be secured at least at a time other than the time of cutting hair 91 in hair cutting device 1, and light irradiator 40 may come into contact with base 51 at the time of cutting hair 91. For example, in the configuration in which optical waveguide 4 is bonded to base 51 with adhesive member 52 only at both ends in the longitudinal direction of base 51, optical waveguide 4 is not bonded to base 51 at the center of base 51 in the longitudinal direction. In such a configuration, at the center of base 51 in the longitudinal direction, optical waveguide 4 only needs to be held in a state of floating from base 51 at a time other than at the time of cutting hair 91 with hair cutting device 1. That is, at the center of base 51 in the longitudinal direction, optical waveguide 4 may be pressed against base 51 by receiving a reaction force from hair 91 at the time of cutting hair 91 with hair cutting device 1, for example.

Light source 21 may generate not only light of a single wavelength but also light of a plurality of wavelengths, for example. In this case, light source 21 may simultaneously generate light of a plurality of wavelengths, or may sequentially generate the light while switching the frequency. In this configuration, since the light (first irradiation light Op1) with which light irradiator 40 irradiates hair 91 can target a plurality of chromophores corresponding to a plurality of wavelengths, it is possible to break bonds of a plurality of types of molecules and to improve cutting efficiency of hair 91.

Hair cutting device 1 may include a plurality of optical waveguides 4. In this case, hair cutting device 1 can cut hair 91 by irradiating hair 91 with light by light irradiator 40 of each of the plurality of optical waveguides 4. Here, the plurality of optical waveguides 4 may pass light of the same wavelength or may pass light of a plurality of different wavelengths.

In the first exemplary embodiment, the operation mode of light source 21 is manually switched between the first mode and the second mode. However, the present invention is not limited to this example, and the operation mode may be automatically switched between the first mode and the second mode. As an example, when the operation mode of light source 21 includes a mixture mode as a third mode in addition to the first mode and the second mode, mode switcher 62 may be able to select the mixture mode (third mode). In the mixture mode (third mode), the first mode and the second mode are periodically and alternately switched, for example. Therefore, when the operation mode of light source 21 is the mixture mode (third mode), light source 21 alternately repeats the first mode in which the time length of light emission period T1 is less than or equal to 1/10000 seconds and the second mode in which the time length of light emission period T1 is more than or equal to 1/100 seconds.

Battery 23 is not limited to a secondary battery, and may be a primary battery. Furthermore, hair cutting system 10 is not limited to the battery-driven type, and may operate by receiving power supply from an external power supply such as a system power supply (commercial power supply), for example. In this case, battery 23 as hair cutting system 10 can be omitted.

The power density of the light passing through optical waveguide 4 may be adjusted by other than the output from light source 21. For example, the power density of the light passing through optical waveguide 4 may be adjusted by optical system 22 or an optical filter included in optical waveguide 4. Alternatively, the power density of the light passing through optical waveguide 4 may be adjusted by changing the radius of curvature of optical waveguide 4. The power density of the light passing through optical waveguide 4 may be adjusted by exposing core 41 from a part of optical waveguide 4 and leaking a part of the light from core 41.

A mirror may be disposed at an end (tip end) of optical waveguide 4 on the opposite side to light receiver 43, and light reaching the tip end of optical waveguide 4 may be reflected by the mirror into optical waveguide 4.

The function of acting on skin 92 is merely a secondary function of hair cutting device 1, and can be omitted as appropriate. That is, hair cutting device 1 only needs to have a function of cutting hair 91, which is a basic function.

Fixing block 32 is not limited to be made of synthetic resin, and may be made of metal, for example.

In a comparison between two values, "more than or equal to" includes both a case where the two values are equal and a case where one of the two values exceeds the other. However, the present invention is not limited to this definition, and "more than or equal to" mentioned here may be synonymous with "more than" including only a case where one of the two values exceeds the other. That is, whether or not to include the case where two values are equal to each other may be changed in any manner depending on settings of threshold values and the like. Accordingly, there is no technical difference between "more than or equal to" and "more than". Similarly, "less than" may be synonymous with "less than or equal to".

Second Exemplary Embodiment

As illustrated in FIGS. 10A and 10B, hair cutting device 1A according to the present exemplary embodiment is different from hair cutting device 1 according to the first exemplary embodiment in the holding structure of optical waveguide 4 with holding member 5. Hereinafter, the same configurations as those of the first exemplary embodiment are denoted by common reference numerals, and the description will be appropriately omitted. Regarding FIG. 10A and the subsequent drawings, in a sectional view of a region of optical waveguide 4 where core 41 is exposed, illustration of cladding 42 existing on the back side of the cross section (paper surface) is omitted.

In hair cutting device 1A according to the present exemplary embodiment, as illustrated in FIG. 10A, optical waveguide 4 (core 41) is disposed biasedly on one end side (negative side of the Z axis) of base 51 in the Z axis direction. That is, in the present exemplary embodiment, the optical axis (central axis) of core 41 is disposed at a position of side face 512 of base 51, the position being closer to the end edge on opposing face 511 (contact surface) as viewed from the center in the shorter direction (Z axis direction). As a result, as compared with the case where the optical axis of core 41 is positioned at the center of side face 512 of base 51 as in the first exemplary embodiment, optical waveguide 4 (core 41) can be brought closer to surface 921 of skin 92 at the time of cutting hair 91. Therefore, according to hair cutting device 1A according to the present exemplary embodiment, hair 91 can be cut at a position closer to the root.

Here, as illustrated in FIG. 10B, in the cross section orthogonal to the longitudinal direction (X axis direction) of base 51, the shape of adhesive member 52 is controlled such that a part of core 41 of optical waveguide 4 is buried in adhesive member 52 and a part of core 41 is exposed from adhesive member 52. More specifically, adhesive member 52 crawls up along the periphery of core 41 due to the "wettability" of core 41 to a height of substantially about ¾ (i.e., three times the radius) of core 41 in the traveling direction (Y axis direction) of hair cutting device 1A. As a result, most of the periphery of core 41 of optical waveguide 4 is covered with adhesive member 52, and the remaining part is exposed from holding member 5 (adhesive member 52) to constitute light irradiator 40. That is, adhesive member 52 covers a region other than light irradiator 40 in optical waveguide 4.

In the present exemplary embodiment, as illustrated in FIG. 10B, the face of adhesive member 52 facing the negative orientation of the Z axis is flush with opposing face 511 of base 51. That is, adhesive member 52 formed so as to cover optical waveguide 4 (core 41) by crawling up along the periphery of core 41 has a face that is flush with opposing face 511, and this face functions as a contact surface that comes into contact with skin 92 at the time of cutting hair 91. Since opposing face 511 is also flush with the face facing the negative orientation of the Z axis of fixing block 32 and second case 30, the contact surface of adhesive member 52 is also flush with the surface facing the negative orientation of the Z axis of fixing block 32 and second case 30.

Similarly to the first exemplary embodiment, optical waveguide 4 is held by holding member 5 such that height L1 of light irradiator 40 from the contact surface (opposing face 511 or the like) becomes less than or equal to 100 μm. Furthermore, in the present exemplary embodiment, height L1 of light irradiator 40 from opposing face 511, which is the contact surface, is more than or equal to 1 μm, and is not zero (0). Here, also in the present exemplary embodiment, the height of positioner 53 from the contact surface may be defined instead of height L1 of light irradiator 40 from the contact surface. In this case, the distance from the contact surface (opposing face 511 or the like) in the Z axis direction to the edge of the groove as positioner 53 is preferably less than or equal to 100 μm. In particular, in the present exemplary embodiment, the height of positioner 53 from the contact surface, i.e., the distance from the contact surface (opposing face 511 or the like) in the Z axis direction to the edge of the groove as positioner 53 is zero (0).

Also in hair cutting device 1A according to the present exemplary embodiment described above, similarly to hair cutting device 1 according to the first exemplary embodiment, holding member 5 holds optical waveguide 4 in an aspect where light irradiator 40 is exposed from at least one face. Even with such a configuration, light irradiator 40 of optical waveguide 4 irradiates hair 91 with first irradiation light Op1 (see FIG. 3B) and skin 92 is irradiated with second irradiation light Op2 (see FIG. 3B).

Moreover, in the present exemplary embodiment, as compared with the first exemplary embodiment, optical waveguide 4 (core 41) can be brought closer to surface 921 of skin 92 at the time of cutting hair 91, and therefore the light from core 41 can be caused to more effectively act on skin 92. That is, according to hair cutting device 1A according to the present exemplary embodiment, when a part of the light with which light irradiator 40 irradiates hair 91 is scattered, skin 92 around hair 91 is easily irradiated with the scattered light as second irradiation light Op2.

Furthermore, in the present exemplary embodiment, the face of adhesive member 52 facing the negative orientation of the Z axis is flush with opposing face 511 and the like of base 51, and functions as a contact surface that comes into contact with skin 92 at the time of cutting hair 91. Therefore, at the time of cutting hair 91, as illustrated in FIG. 10A, adhesive member 52 comes into contact with surface 921 of skin 92, and adhesive member 52 is held between core 41 of optical waveguide 4 and surface 921 of skin 92. In other words, adhesive member 52 is interposed between core 41 of optical waveguide 4 and skin 92.

Therefore, in hair cutting device 1A, light is attenuated by adhesive member 52 as compared with a case where core 41 comes into direct contact with skin 92, and the power density of the light with which core 41 irradiates skin 92 is easily adjusted appropriately. Specifically, the power density of the light with which core 41 irradiates skin 92 is adjusted by the difference in refractive index between core 41 and adhesive member 52 and the difference in refractive index between adhesive member 52 and surface 921 of skin 92. In the present exemplary embodiment, since the refractive index of adhesive member 52 is smaller than the refractive index of core 41 (light irradiator 40), the amount of light leakage from core 41 to adhesive member 52 can be suppressed to be relatively small. As a result, hair cutting system 10 using hair cutting device 1A can sufficiently suppress damage to skin 92 even when the operation mode of light source 21 is the second mode in which cutting of hair 91 is prioritized, for example.

FIGS. 11A and 11B illustrate hair cutting device 1A according to a modification of the second exemplary embodiment. Hair cutting device 1A according to the modification is different from hair cutting device 1A according to the second exemplary embodiment in that a height of light irradiator 40 from surface 921 of skin 92 is variable. Thus, just like a trimmer, hair cutting device 1A can adjust the position of the cut surface of hair 91 when cutting hair 91, i.e., the length of uncut hair 91.

That is, in the example illustrated in FIG. 11A, hair cutting device 1A includes attachment 33A detachably attached to second case 30 of head 3, thereby increasing the height of light irradiator 40 from surface 921 of skin 92. That is, when attachment 33A is attached to the face of fixing block 32 and second case 30 facing the negative orientation of the Z axis, the height of light irradiator 40 from surface 921 of skin 92 increases by the thickness of attachment 33A. Attachment 33A includes a plurality of comb teeth 331 (only one comb tooth is illustrated in FIGS. 11A and 11B) protruding forward (negative orientation of the Y axis) in the traveling direction of hair cutting device 1A. The plurality of comb teeth 331 are arranged side by side in the longitudinal direction (X axis direction) of light irradiator 40. Hair cutting device 1A can cut hair 91 by guiding hair 91 between a pair of adjacent comb teeth 331 among the plurality of comb teeth 331.

In hair cutting device 1A illustrated in FIG. 11A, the contact surface that comes into contact with skin 92 at the time of cutting hair 91 is not opposing face 511 of base 51 or the like, but is a face of attachment 33A facing the negative orientation of the Z axis. In this example, height L2 of light irradiator 40 from the contact surface (face in attachment 33A facing the negative orientation of the Z axis) becomes larger than height L1 (see FIG. 10B) in the second exemplary embodiment.

In the example illustrated in FIG. 11B, hair cutting device 1A includes attachment 33B detachably attached to second case 30 of head 3, thereby increasing the height of light irradiator 40 from surface 921 of skin 92. Attachment 33B has a configuration common to attachment 33A except that its thickness is larger than that of attachment 33A. Therefore, in the example of FIG. 11B, height L3 of light irradiator 40 from the contact surface (face of the attachment 33B facing the negative orientation of the Z axis) is larger than height L2 (see FIG. 11A).

In the examples illustrated in FIGS. 11A and 11B, attachments 33A and 33B are detachably attached to second case 30, but the present invention is not limited to this configuration. For example, attachments 33A and 33B may change the height of light irradiator 40 from surface 921 of skin 92 by sliding with respect to second case 30.

Various configurations (including modifications) described in the second exemplary embodiment can be adopted in appropriate combination with various configurations (including modifications) described in the first exemplary embodiment.

Third Exemplary Embodiment

Figure 12B:
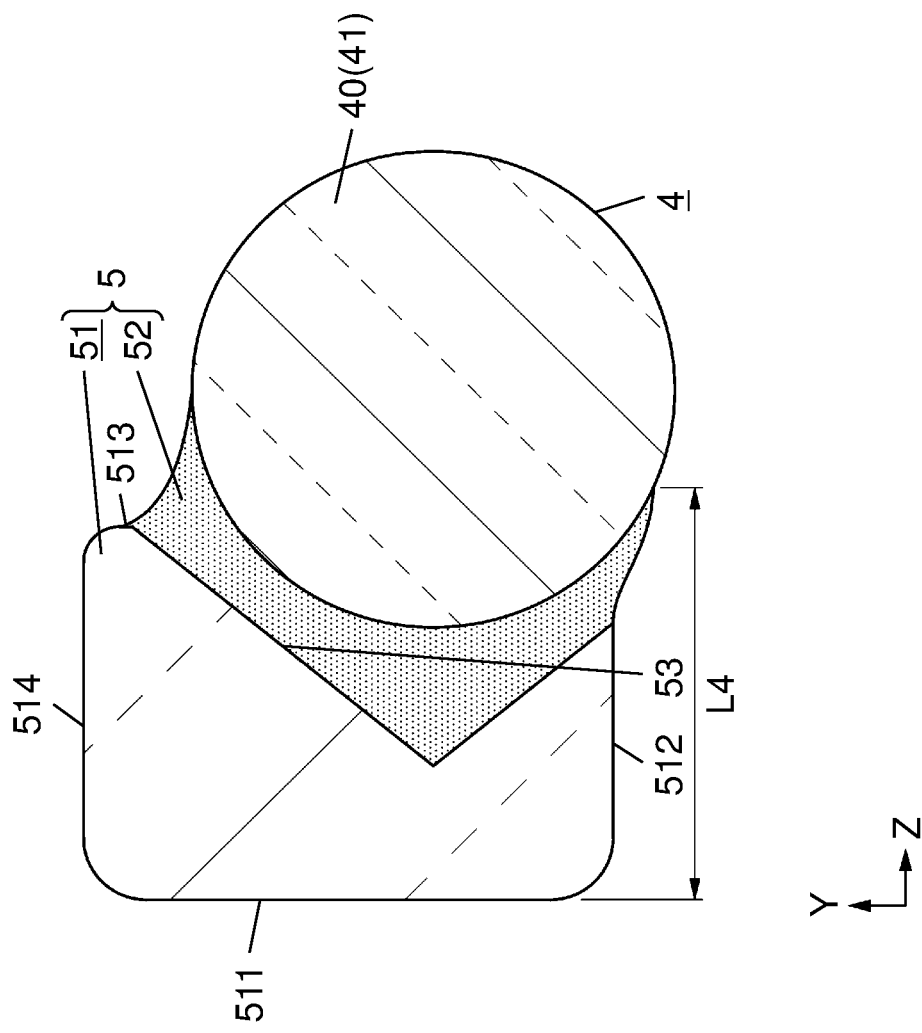
FIG. 12B is an enlarged view of the main part of FIG. 12A.
Figure 12A:
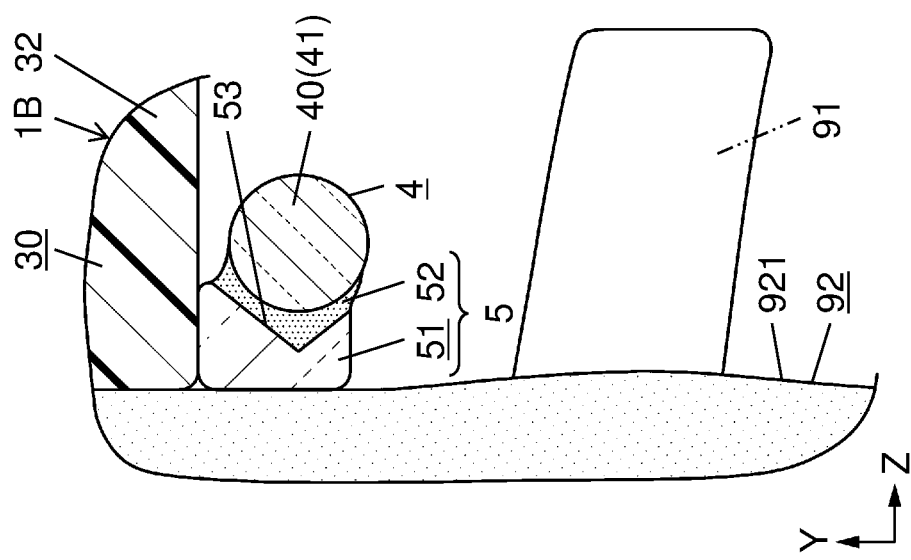
FIG. 12A is a schematic sectional view illustrating a configuration of a main part of a hair cutting device according to a third exemplary embodiment.

As illustrated in FIGS. 12A and 12B, hair cutting device 1B according to the present exemplary embodiment is different from hair cutting device 1 according to the first exemplary embodiment in the holding structure of optical waveguide 4 with holding member 5. Hereinafter, the same configurations as those of the first exemplary embodiment are denoted by common reference numerals, and the description will be appropriately omitted.

In hair cutting device 1B according to the present exemplary embodiment, as illustrated in FIGS. 12A and 12B, optical waveguide 4 is held on back face 513 of opposing face 511, side face 512, back face 513, and rear face 514 of base 51. That is, optical waveguide 4 is held not by side face 512 of base 51 as in the first exemplary embodiment but by back face 513 of base 51. That is, in the present exemplary embodiment, holding member 5 has back face 513 facing an opposite side to opposing face 511 opposing surface 921 of skin 92 at the time of cutting hair 91. Optical waveguide 4 is held by back face 513 of holding member 5. In particular, on base 51, back face 513 is a face along the traveling direction (Y axis direction) of hair cutting device 1B, and is a face facing the positive orientation of the Z axis. Therefore, light irradiator 40 of optical waveguide 4 is fixed to the face (face facing the positive orientation of the Z axis) of holding member 5 along the traveling direction of hair cutting device 1B.

In the present exemplary embodiment, positioner 53 that positions optical waveguide 4 is formed on back face 513 of base 51 where optical waveguide 4 is held. Positioner 53 includes a groove formed on back face 513 of base 51. Optical waveguide 4 is held on back face 513 of base 51 with adhesive member 52 such that at least a part of core 41 exposed by removing cladding 42 is accommodated in the groove serving as positioner 53.

Furthermore, in hair cutting device 1B according to the present exemplary embodiment, optical waveguide 4 (core 41) is disposed biasedly on one end side (negative side of the Y axis) of base 51 in the Y axis direction. That is, in the present exemplary embodiment, the optical axis (central axis) of core 41 is disposed at a position of back face 513 of base 51, the position being closer to the end edge on the front (negative orientation of the Y axis) side in the traveling direction of hair cutting device 1B as viewed from the center in the shorter direction (Y axis direction). As a result, in holding member 5, while optical waveguide 4 is held on back face 513 of base 51, light irradiator 40 easily comes into contact with hair 91 at the time of cutting hair 91.

Also in the present exemplary embodiment, it is preferable that optical waveguide 4 is held by holding member 5 such that height L4 of light irradiator 40 from the contact surface (opposing face 511) in contact with skin 92 at the time of cutting hair 91 becomes less than or equal to 100 μm. However, since base 51 is interposed between core 41 and the contact surface (opposing face 511), height L4 of light irradiator 40 from opposing face 511, which is the contact surface, is more than or equal to 1 μm, and is not zero (0).

Also in hair cutting device 1B according to the present exemplary embodiment described above, similarly to hair cutting device 1 according to the first exemplary embodiment, holding member 5 holds optical waveguide 4 in an aspect where light irradiator 40 is exposed from at least one face. Even with such a configuration, light irradiator 40 of optical waveguide 4 irradiates hair 91 with first irradiation light Op1 (see FIG. 3B) and skin 92 is irradiated with second irradiation light Op2 (see FIG. 3B).

Moreover, in the present exemplary embodiment, base 51 is interposed between optical waveguide 4 (core 41) and surface 921 of skin 92. Therefore, skin 92 can be irradiated with the light leaking from core 41 to adhesive member 52 through base 51. Here, light is attenuated by adhesive member 52 and base 51, and the power density of the light with which core 41 irradiates skin 92 is easily adjusted appropriately. Specifically, the power density of the light with which core 41 irradiates skin 92 is adjusted by the difference in refractive index between core 41 and adhesive member 52, the difference in refractive index between adhesive member 52 and base 51, and the difference in refractive index between base 51 and surface 921 of skin 92.

Figure 13:
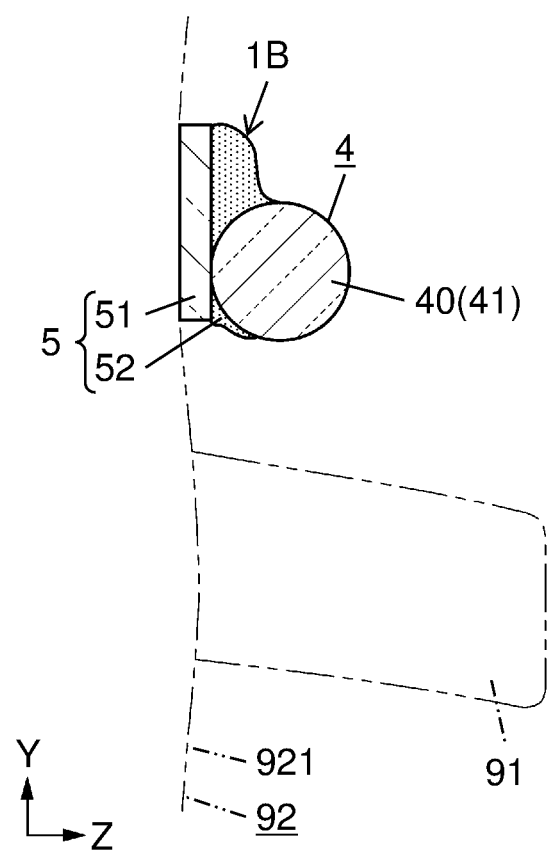
FIG. 13 is a schematic sectional view illustrating a configuration of a main part of a hair cutting device according to a modification of the third exemplary embodiment.

FIG. 13 illustrates hair cutting device 1B according to a modification of the third exemplary embodiment. Hair cutting device 1B according to the modification is different from hair cutting device 1B according to the third exemplary embodiment in that base 51 is a sheet material. Here, as an example, it is assumed that the sheet material as base 51 is a flexible synthetic resin sheet.

In the present modification, the refractive index of the sheet material as base 51 is smaller than the refractive index of light irradiator 40. That is, if the refractive index of light irradiator 40 (core 41) is "1.4698", the refractive index of the sheet material as base 51 is smaller than "1.4698". Here, as an example, the refractive index of base 51 (sheet material) is substantially the same as the refractive index of cladding 42.

Furthermore, in hair cutting device 1B illustrated in FIG. 13, since base 51 is a sheet material, a groove as positioner 53 (see FIG. 12B) is omitted, and optical waveguide 4 is bonded to one surface (one face in the thickness direction) of flat base 51 with adhesive member 52. That is, in hair cutting device 1B according to the present modification, base 51 is a sheet material, and optical waveguide 4 is held with adhesive member 52 on one face in the thickness direction of the sheet material.

According to the present modification, as compared with hair cutting device 1B of the third exemplary embodiment, optical waveguide 4 (core 41) can be brought closer to surface 921 of skin 92 at the time of cutting hair 91. Therefore, according to hair cutting device 1B of the present modification, hair 91 can be cut at a position closer to the root. The power density of the light with which core 41 irradiates skin 92 can be adjusted by the difference in refractive index between core 41 and adhesive member 52, the difference in refractive index between adhesive member 52 and base 51 (sheet material), and the difference in refractive index between base 51 (sheet material) and surface 921 of skin 92.

Various configurations (including modifications) described in the third exemplary embodiment can be adopted in appropriate combination with various configurations (including modifications) described in the first exemplary embodiment or the second exemplary embodiment.

Fourth Exemplary Embodiment

Figure 14A:
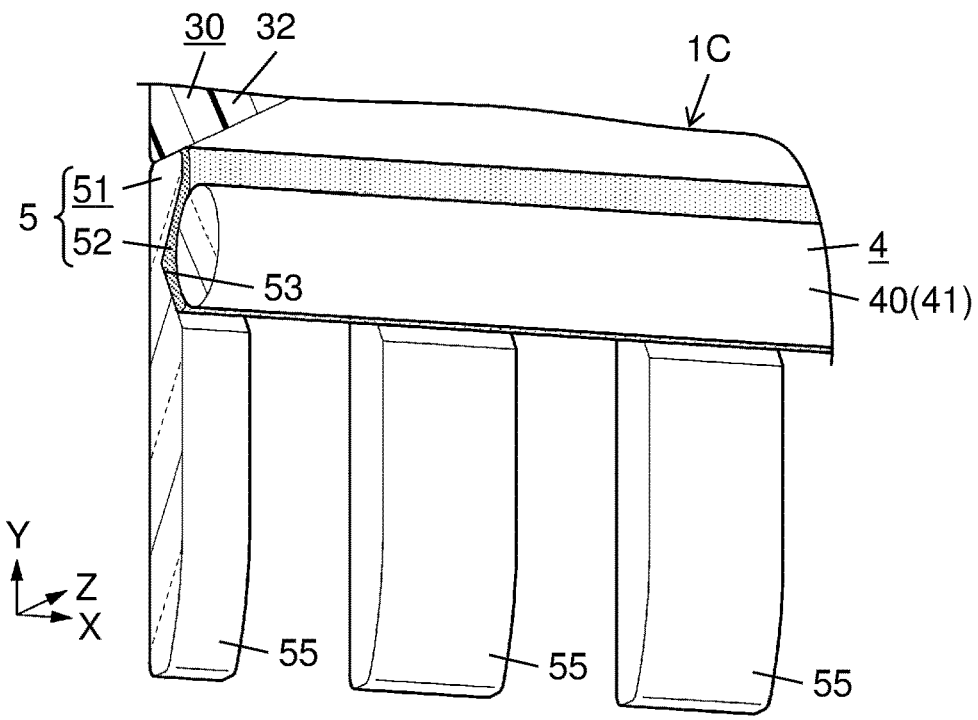
FIG. 14A is a schematic perspective view of a main part of the hair cutting device according to the third exemplary embodiment when the hair cutting device is viewed from one direction.
Figure 14B:
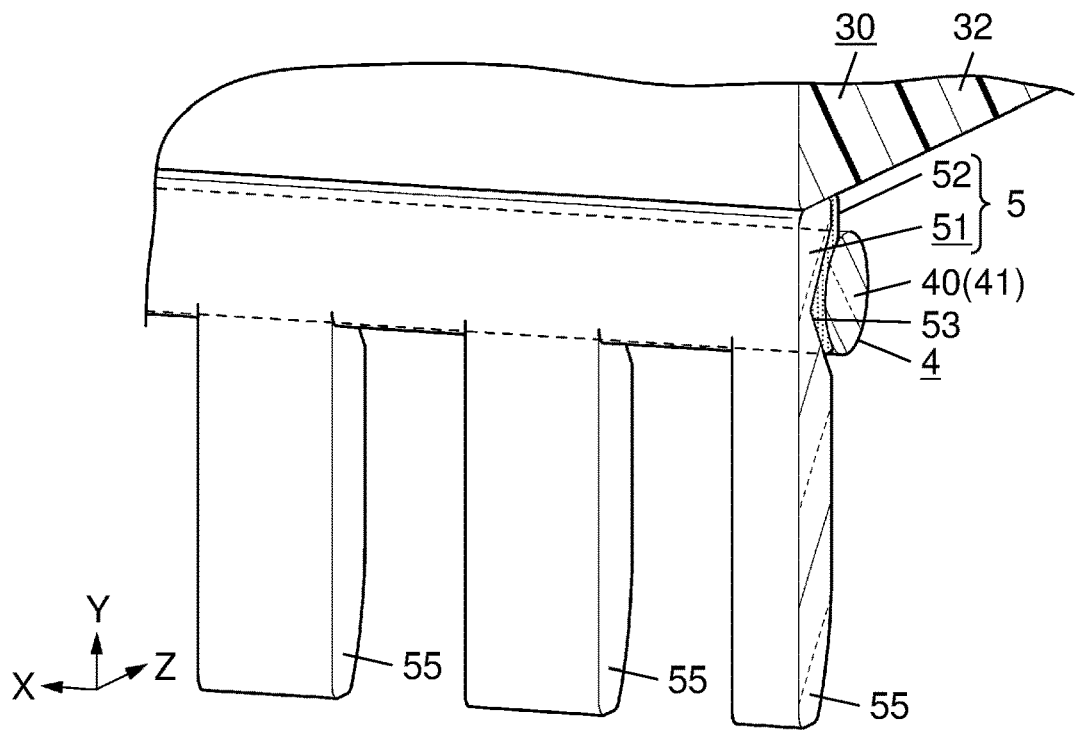
FIG. 14B is a schematic perspective view of the main part of the hair cutting device according to the third exemplary embodiment when the hair cutting device is viewed from another direction.

As illustrated in FIGS. 14A and 14B, hair cutting device 1C according to the present exemplary embodiment is different from hair cutting device 1 according to the third exemplary embodiment in the shape of holding member 5. Hereinafter, the same configurations as those of the third exemplary embodiment are denoted by common reference numerals, and the description will be appropriately omitted.

In the present exemplary embodiment, base 51 includes a plurality of protrusions 55 that protrude forward (negative orientation of the Y axis) in the traveling direction of hair cutting device 1C. The plurality of protrusions 55 are arranged side by side in the longitudinal direction (X axis direction) of light irradiator 40. In the present exemplary embodiment, as an example, base 51 and the plurality of protrusions 55 are a resin molded product integrally formed in an inseparable aspect. Here, faces of the plurality of protrusions 55 facing the negative orientation of the Z axis are flush with opposing face 511 (see FIG. 12B), which is a face of base 51 facing the negative orientation of the Z axis. Therefore, in hair cutting device 1C, the contact surface that comes into contact with skin 92 at the time of cutting hair 91 is opposing face 511 of base 51 and the faces of the plurality of protrusions 55 facing the negative orientation of the Z axis.

Also in hair cutting device 1C according to the present exemplary embodiment, similarly to the third exemplary embodiment, optical waveguide 4 is held on back face 513 (see FIG. 12B) of base 51 facing the positive orientation of the Z axis, which is a face along the traveling direction (Y axis direction) of hair cutting device 1C. Therefore, optical waveguide 4 is held with adhesive member 52 near roots of the plurality of protrusions 55 on back face 513 of base 51 so as to expose light irradiator 40. In other words, the plurality of protrusions 55 protrude from side face 512 (see FIG. 12B) of base 51 intersecting surface 921 of skin 92 at the time of cutting hair 91. Light irradiator 40 held on base 51 is exposed from side face 512 of base 51 and between the pair of adjacent protrusions 55.

Figure 15:
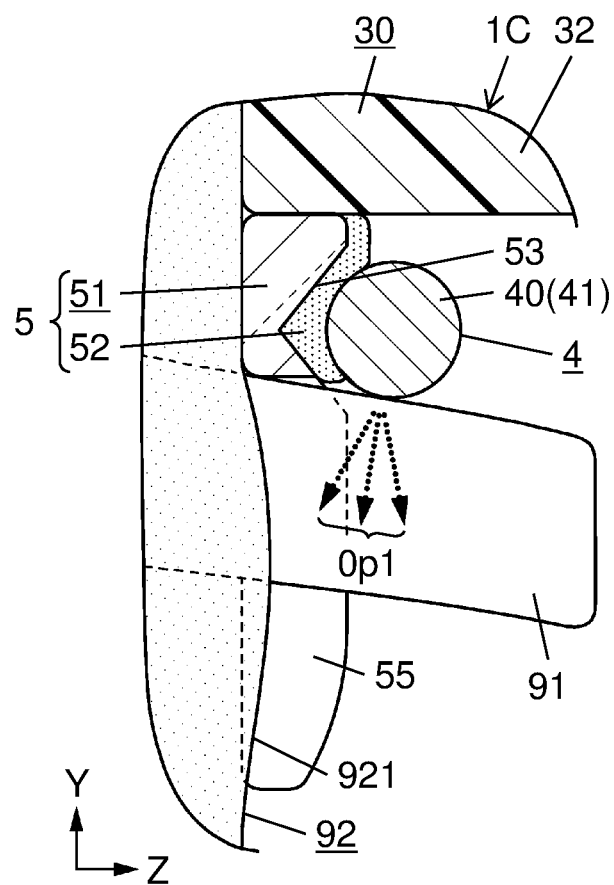
FIG. 15 is a schematic sectional view illustrating a configuration of the main part of the hair cutting device.

In hair cutting device 1C according to the present exemplary embodiment described above, at the time of cutting hair 91, as illustrated in FIG. 15, it is possible to cut hair 91 by guiding hair 91 between a pair of adjacent protrusions 55 among the plurality of protrusions 55. That is, since light irradiator 40 of optical waveguide 4 held on base 51 is exposed between the pair of protrusions 55, light irradiator 40 comes into contact with hair 91 guided between the pair of protrusions 55, and light irradiator 40 irradiates hair 91 with first irradiation light Op1 to cut hair 91.

That is, in the present exemplary embodiment, holding member 5 has the plurality of protrusions 55. The plurality of protrusions 55 protrude from one face (side face 512) that intersects surface 921 of skin 92 at the time of cutting hair 91 and is a face (side face 512) on which light irradiator 40 is exposed. Light irradiator 40 irradiates hair 91 introduced between the pair of adjacent protrusions 55 in the plurality of protrusions 55 with light. Therefore, light irradiator 40 does not come into contact with hair 91 over the entire length in the longitudinal direction, but can come into contact with hair 91 only with a part exposed from between the pair of adjacent protrusions 55. As a result, in hair cutting device 1C, the amount of light leaking from light irradiator 40 to hair 91 when light irradiator 40 comes into contact with hair 91 can be suppressed, and the loss of light passing through optical waveguide 4 can be suppressed to be small.

Also in hair cutting device 1C according to the present exemplary embodiment, light irradiator 40 irradiates skin 92 with second irradiation light Op2 (see FIG. 3B). However, a part of second irradiation light Op2 is blocked by each of the plurality of protrusions 55, and does not reach skin 92. That is, since second irradiation light Op2 from light irradiator 40 does not directly reach the part of skin 92 that becomes shadow of the plurality of protrusions 55 as viewed from light irradiator 40, the energy of the light with which skin 92 is irradiated is easily adjusted to an appropriate level. In other words, since skin 92 is locally irradiated with second irradiation light Op2 from the gap between the pair of adjacent protrusions 55, the energy of the light with which skin 92 is irradiated can be suppressed to be small as compared with the case where a wide range of skin 92 is irradiated with the light.

Figure 16A:
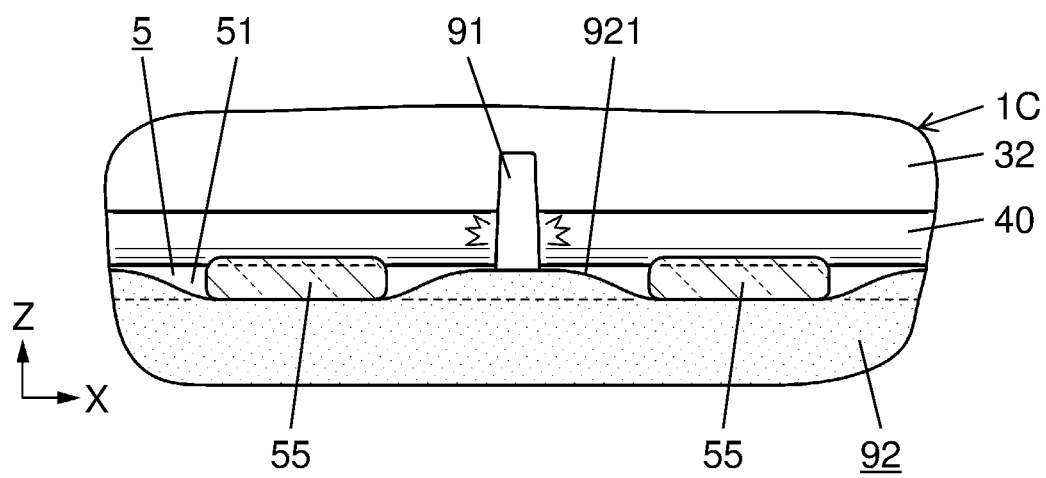
FIG. 16A is a schematic view illustrating a configuration of the main part of the hair cutting device as the main part is viewed from front in a traveling direction.
Figure 16B:
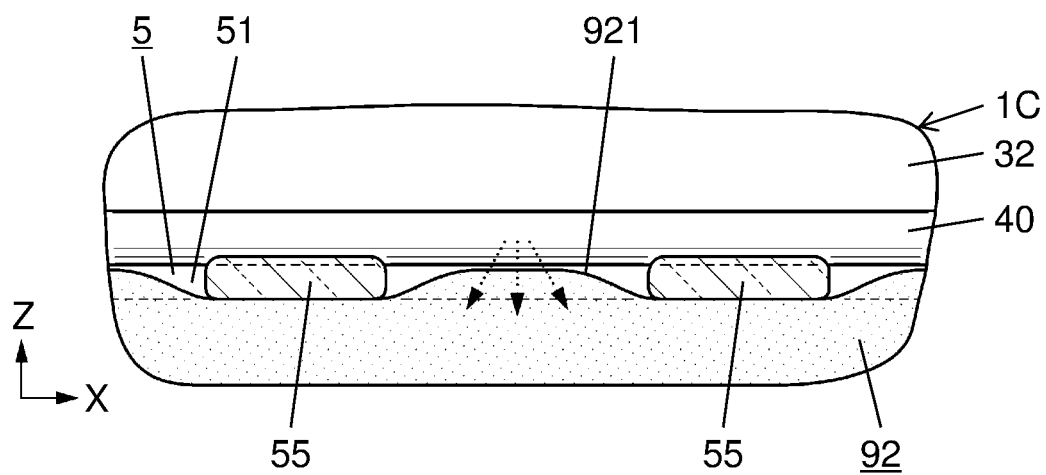
FIG. 16B is a schematic view illustrating a configuration of the main part of the hair cutting device as the main part is viewed from front in the traveling direction.

Furthermore, as illustrated in FIGS. 16A and 16B, hair cutting device 1C according to the present exemplary embodiment can partially press skin 92 with the plurality of protrusions 55 at the time of cutting hair 91. FIGS. 16A and 16B are schematic views illustrating the configuration around optical waveguide 4 and holding structure 5 when viewed from the front (negative orientation of the Y axis) in the traveling direction of hair cutting device 1C at the time of cutting hair 91.

That is, as illustrated in FIG. 16A, when skin 92 on both sides of hair 91 to be cut is pressed by the pair of protrusions 55, skin 92 around hair 91 exposed from between the pair of protrusions 55 is raised. Therefore, according to hair cutting device 1C, hair 91 can be cut at a position closer to the root. Moreover, also regarding the action on skin 92, as illustrated in FIG. 16B, skin 92 raised between the pair of protrusions 55 approaches light irradiator 40 and easily comes into contact with light irradiator 40, so that light irradiator 40 also efficiently irradiates skin 92 with light.

As a modification of the fourth exemplary embodiment, the shape of the plurality of protruding portions 55 can be changed as appropriate. For example, each of the plurality of protruding portions 55 is not limited to a linear shape in a plan view (as viewed from one side of the Z axis), and any shape such as a rectangular shape, a trapezoidal shape, a triangular shape, a semicircular shape, or a curved shape can be adopted.

Various configurations (including modifications) described in the fourth exemplary embodiment can be adopted in appropriate combination with various configurations (including modifications) described in the first exemplary embodiment, the second exemplary embodiment, or the third exemplary embodiment.

Conclusions

As described above, hair cutting device (1 or 1A to 1C) according to the first aspect includes optical waveguide (4, 4A, or 4B). Optical waveguide (4, 4A, or 4B) includes light irradiator (40). Light irradiator (40) cuts hair (91) by irradiating hair (91) protruding from skin (92) with light. The refractive index of light irradiator (40) is smaller than the refractive index of surface (921) of skin (92).

According to this aspect, since the refractive index of light irradiator (40) is smaller than the refractive index of surface (921) of skin (92), options such as the material of optical waveguide (4, 4A, or 4B) including light irradiator (40) increase, and hair cutting device (1 or 1A to 1C) becomes easily achieved. Furthermore, according to hair cutting device (1 or 1A to 1C), for example, when skin (92) is appropriately irradiated with light from light irradiator (40), an action on skin (92) such as sterilization or activation can also be expected. As a result, there is an advantage of providing improved hair cutting device (1 or 1A to 1C).

In hair cutting device (1 or 1A to 1C) according to the second aspect, in the first aspect, the refractive index of surface (921) of skin (92) is smaller than the refractive index of hair (91).

According to this aspect, it is possible to efficiently irradiate hair (91) having a refractive index larger than that of surface (921) of skin (92) with light from light irradiator (40).

In hair cutting device (1 or 1A to 1C) according to the third aspect, in the first or second aspect, optical waveguide (4, 4A, or 4B) includes core (41). Light irradiator (40) is formed of core (41).

According to this aspect, a general optical fiber or the like having core (41) can be used as optical waveguide (4, 4A, or 4B).

In hair cutting device (1 or 1A to 1C) according to the fourth aspect, in the third aspect, optical waveguide (4, 4A, or 4B) further includes cladding (42). Cladding (42) covers at least a part of core (41). Light irradiator (40) includes a region that is a part of core (41) in the circumferential direction and exposed from cladding (42).

According to this aspect, it is possible to efficiently propagate light in optical waveguide (4, 4A, or 4B) using total reflection at the interface between core (41) and cladding (42).

In hair cutting device (1 or 1A to 1C) according to the fifth aspect, in any of the first to fourth aspects, the refractive index of light irradiator (40) is less than or equal to 1.47.

According to this aspect, the refractive index of light irradiator (40) can be set smaller than the refractive index of surface (921) of general human skin (92).

Hair cutting system (10) according to the sixth aspect includes hair cutting device (1 or 1A to 1C) according to any of the first to fifth aspects and light source (21) that generates light to be input to optical waveguide (4, 4A, or 4B).

According to this aspect, there is an advantage of providing improved hair cutting system (10).

In hair cutting system (10) according to the seventh aspect, in the sixth aspect, light source (21) intermittently generates light by repeating light emission period (T1) and light-off period (T2).

According to this aspect, consumption of electric energy in light source (21) can be suppressed.

In hair cutting system (10) according to the eighth aspect, in the seventh aspect, the time length of light emission period (T1) is less than or equal to 1/10000 seconds.

According to this aspect, it is possible to irradiate with light having energy suitable for an action on skin (92).

In hair cutting system (10) according to the ninth aspect, in the seventh aspect, the time length of light emission period (T1) is more than or equal to 1/100 seconds.

According to this aspect, it is possible to irradiate with light having energy suitable for cutting hair (91).

In hair cutting system (10) according to the tenth aspect, in the seventh aspect, the operation mode of light source (21) is switchable between the first mode and the second mode. In the first mode, the time length of light emission period (T1) is less than or equal to 1/10000 seconds. In the second mode, the time length of light emission period (T1) is more than or equal to 1/100 seconds.

According to this aspect, it is possible to switch between irradiation with light of energy suitable for an action on skin (92) and irradiation with light of energy suitable for cutting hair (91).

In hair cutting system (10) according to the eleventh aspect, in any of the seventh to tenth aspects, the wavelength of light generated by light source (21) is more than or equal to 400 nm.

According to this aspect, it is possible to irradiate with light having a wavelength suitable for an action on skin (92).

In hair cutting system (10) according to the twelfth aspect, in any of the seventh to eleventh aspects, light source (21) is a laser light source.

According to this aspect, it is possible to irradiate with light having energy suitable for cutting hair (91).

The configuration according to the second to fifth aspects is not an essential configuration to hair cutting device (1 or 1A to 1C), and can be omitted as appropriate.

The configuration according to the seventh to twelfth aspects is not an essential configuration to hair cutting system (10), and can be omitted as appropriate.

INDUSTRIAL APPLICABILITY

The hair cutting device and the hair cutting system can be applied to cutting of various hairs of a human or an animal other than a human in various fields such as home use, beauty, medical care, or nursing care.

REFERENCE MARKS IN THE DRAWINGS

1, 1A to 1C: hair cutting device
4, 4A, 4B: optical waveguide
10: hair cutting system
21: light source
40: light irradiator
41: core
42: cladding
91: hair
92: skin
921: surface
T1: light emission period
T2: light-off period

The invention claimed is:

1. A hair cutting device, comprising:
an optical waveguide, wherein:
the optical waveguide comprises a light irradiator for irradiating hair protruding from a skin with light to cut the hair,
the optical waveguide has a core,
the light irradiator is formed of the core,
the optical waveguide further comprises cladding that covers at least a part of the core,
a refractive index of the light irradiator is smaller than a refractive index of a surface of the skin,
the following relationship is satisfied:
a refractive index of the cladding<a refractive index of the core<a refractive index of a surface of the skin<a refractive index of the hair, and
the refractive index of the light irradiator is less than or equal to 1.47.

2. The hair cutting device according to claim 1, wherein the light irradiator comprises a region that is a part of the core in a circumferential direction and is exposed from the cladding.

3. A hair cutting system comprising:
the hair cutting device according to claim 1; and
a light source for generating light to be input to the optical waveguide.

4. The hair cutting system according to claim 3, wherein the light source intermittently generates the light by repeating a light emission period and a light-off period.

5. The hair cutting system according to claim 4, wherein a time length of the light emission period is less than or equal to 1/10000 seconds.

6. The hair cutting system according to claim 4, wherein a time length of the light emission period is more than or equal to 1/100 seconds.

7. The hair cutting system according to claim 4, wherein an operation mode of the light source is switchable between a first mode in which a time length of the light emission period is equal to or less than 1/10000 seconds, and a second mode in which a time length of the light emission period is more than or equal to 1/100 seconds.

8. The hair cutting system according to claim 4, wherein a wavelength of light generated by the light source is more than or equal to 400 nm.

9. The hair cutting system according to claim 4, wherein the light source is a laser light source.

* * * * *